(12) United States Patent
Nelson et al.

(10) Patent No.: US 12,257,238 B2
(45) Date of Patent: Mar. 25, 2025

(54) MAGNESIUM BIOTINATE COMPOSITIONS AND METHODS OF USE

(71) Applicant: Nutrition21, LLC, Saddle Brook, NJ (US)

(72) Inventors: Deanna J. Nelson, Raleigh, NC (US); James R. Komorowski, Trumbull, CT (US)

(73) Assignee: Nutrition21, LLC, Saddle Brook, NJ (US)

( * ) Notice: Subject to any disclaimer, the term of this patent is extended or adjusted under 35 U.S.C. 154(b) by 0 days.

(21) Appl. No.: 18/441,413

(22) Filed: Feb. 14, 2024

(65) Prior Publication Data
US 2024/0299364 A1    Sep. 12, 2024

Related U.S. Application Data

(60) Continuation of application No. 16/855,966, filed on Apr. 22, 2020, now Pat. No. 11,931,342, which is a
(Continued)

(51) Int. Cl.
*A61K 31/4188* (2006.01)
*A61G 3/00* (2006.01)
(Continued)

(52) U.S. Cl.
CPC .......... *A61K 31/4188* (2013.01); *A61K 8/19* (2013.01); *A61K 8/673* (2013.01); *A61K 9/0053* (2013.01);
(Continued)

(58) Field of Classification Search
CPC . A61K 8/19; A61K 8/673; A61K 9/28; A61K 9/0053; A61K 9/2086; A61K 9/2806; A61K 31/4188; A61K 2800/58; A61P 1/14; A61P 3/00; A61P 15/08; A61P 17/00; A61P 7/06; A61P 17/14; A61P 21/00;
(Continued)

(56) References Cited

U.S. PATENT DOCUMENTS 3,337,403 A    8/1967    Zentner
4,277,488 A    7/1981    Mitsunaga et al.
(Continued)

FOREIGN PATENT DOCUMENTS

CN    1842318 A    10/2006
EP    056902 A2    8/1982
(Continued)

OTHER PUBLICATIONS

Adams et al., "Effect of a vitamin/mineral supplement on children and adults with autism," BMC Pediatrics, Dec. 2011; 11 (111), [retrieved on Oct. 8, 2019]. Retrieved from the Internet: <URL: https://bmcpediatr.biomedcentral.com/track/pdf/10.1186/1471-2431-11-111>.
(Continued)

*Primary Examiner* — Hong Yu
(74) *Attorney, Agent, or Firm* — Foley Hoag LLP; Lucas P. Watkins; Benjamin A. Vaughan

(57) ABSTRACT

The present application relates to magnesium biotinate compositions and methods of use. The methods and compositions disclosed herein are particularly useful for providing bioavailable biotin to mammals and treating or preventing symptoms of biotin deficiency.

7 Claims, 6 Drawing Sheets

Related U.S. Application Data division of application No. 15/693,223, filed on Aug. 31, 2017, now Pat. No. 11,938,117.

(60) Provisional application No. 62/382,438, filed on Sep. 1, 2016.

(51) Int. Cl.

| | |
|---|---|
| *A61K 8/19* | (2006.01) |
| *A61K 8/67* | (2006.01) |
| *A61K 9/00* | (2006.01) |
| *A61K 9/20* | (2006.01) |
| *A61K 9/28* | (2006.01) |
| *A61Q 3/00* | (2006.01) |
| *A61Q 5/00* | (2006.01) |
| *A61Q 7/00* | (2006.01) |

(52) U.S. Cl.
CPC .............. *A61K 9/2086* (2013.01); *A61K 9/28* (2013.01); *A61K 9/2806* (2013.01); *A61Q 3/00* (2013.01); *A61Q 5/002* (2013.01); *A61Q 7/00* (2013.01); *A61K 2800/58* (2013.01)

(58) Field of Classification Search
CPC ......... A61P 25/24; A61P 25/32; A61P 25/00; A61P 29/00; A61P 31/04; A61P 31/10; A61P 7/08; A61P 43/00; A61Q 3/00; A61Q 5/002; A61Q 7/00
See application file for complete search history.

(56) References Cited

U.S. PATENT DOCUMENTS

| | | | |
|---|---|---|---|
| 4,297,349 A | 10/1981 | Barcza | |
| 4,385,052 A | 5/1983 | Zackheim et al. | |
| 4,573,996 A | 3/1986 | Kwiatek et al. | |
| 4,597,961 A | 7/1986 | Etscorn | |
| 4,725,427 A | 2/1988 | Ashmead et al. | |
| 4,839,174 A | 6/1989 | Baker et al. | |
| 4,847,082 A | 7/1989 | Sabin | |
| 4,908,213 A | 3/1990 | Govil et al. | |
| 4,943,435 A | 7/1990 | Baker et al. | |
| 5,166,168 A | 11/1992 | Stiefel | |
| 5,217,997 A | 6/1993 | Levere et al. | |
| 5,250,569 A | 10/1993 | Godfrey | |
| 5,284,657 A | 2/1994 | Lu et al. | |
| 5,288,497 A | 2/1994 | Stanley et al. | |
| 5,550,249 A | 8/1996 | Della Valle et al. | |
| 5,622,980 A | 4/1997 | Caldwell et al. | |
| 5,626,884 A | 5/1997 | Lockett | |
| 5,656,264 A | 8/1997 | Hanada et al. | |
| 5,662,920 A | 9/1997 | Santus | |
| 5,707,970 A | 1/1998 | McCarty et al. | |
| 5,716,610 A | 2/1998 | Jack et al. | |
| 5,763,392 A | 6/1998 | Hansen et al. | |
| 5,763,496 A | 6/1998 | Holland | |
| 5,804,203 A | 9/1998 | Hahn et al. | |
| 5,840,881 A | 11/1998 | Uda et al. | |
| 6,066,659 A | 5/2000 | Speck | |
| 6,123,936 A | 9/2000 | Platz et al. | |
| 6,132,394 A | 10/2000 | Lankinen | |
| 6,156,735 A | 12/2000 | McCarty et al. | |
| 6,182,655 B1 | 2/2001 | Keller et al. | |
| 6,207,713 B1 | 3/2001 | Fossel | |
| 6,298,847 B1 | 10/2001 | Datta et al. | |
| 6,344,444 B1 | 2/2002 | McCarty et al. | |
| 6,387,394 B1 | 5/2002 | Baichwal et al. | |
| 6,418,926 B1 | 7/2002 | Chawla | |
| 6,462,051 B1 | 10/2002 | Nozawa et al. | |
| 6,660,251 B1 | 12/2003 | Bunger et al. | |
| 6,709,868 B2 | 3/2004 | Law et al. | |
| 6,803,456 B1 | 10/2004 | Kuhlmann | |
| 7,238,373 B2 | 7/2007 | Meyrowitz | |
| 7,576,132 B2 | 8/2009 | Juturu et al. | |
| 8,524,279 B2 | 9/2013 | Snyder et al. | |
| 8,779,007 B2 | 7/2014 | Kropke et al. | |
| 8,835,487 B2 | 9/2014 | Sedel | |
| 9,339,467 B2 | 5/2016 | Beyerinnck et al. | |
| 9,351,961 B2 | 5/2016 | Sedel | |
| 10,959,971 B2 | 3/2021 | Komorowski | |
| 11,246,886 B2 | 2/2022 | Komorowski | |
| 11,850,219 B2 | 12/2023 | Komorowski | |
| 11,931,342 B2 | 3/2024 | Nelson | |
| 11,938,117 B2 | 3/2024 | Nelson | |
| 2002/0068365 A1 | 6/2002 | Kuhrts | |
| 2002/0123504 A1 | 9/2002 | Redmon et al. | |
| 2002/0132800 A1 | 9/2002 | Popp et al. | |
| 2003/0028169 A1 | 2/2003 | Fossel | |
| 2004/0009746 A1 | 1/2004 | Korman | |
| 2004/0097467 A1 | 5/2004 | Juturu et al. | |
| 2004/0204387 A1 | 10/2004 | McLaurin | |
| 2005/0048012 A1 | 3/2005 | Jermann et al. | |
| 2006/0020007 A1 | 1/2006 | Berlin | |
| 2006/0115555 A1 | 6/2006 | Foulger et al. | |
| 2006/0204455 A1 | 9/2006 | Giniger | |
| 2007/0020206 A1 | 1/2007 | Jermann et al. | |
| 2007/0116831 A1 | 5/2007 | Prakash et al. | |
| 2007/0149442 A1 | 6/2007 | Rubin | |
| 2007/0292493 A1 | 12/2007 | Brierre | |
| 2009/0104171 A1 | 4/2009 | Pardee et al. | |
| 2010/0291195 A1 | 11/2010 | Fossel | |
| 2011/0123553 A1 | 5/2011 | Mi et al. | |
| 2012/0064126 A1 | 3/2012 | Sung et al. | |
| 2012/0141588 A1 | 6/2012 | Chopra et al. | |
| 2012/0238498 A1 | 9/2012 | Endo | |
| 2013/0101569 A1 | 4/2013 | Weston | |
| 2013/0296390 A1 | 11/2013 | Nelson | |
| 2014/0011255 A1 | 1/2014 | Ying et al. | |
| 2014/0030331 A1 | 1/2014 | Sedel | |
| 2014/0364461 A1 | 12/2014 | Karnik | |
| 2016/0000809 A1 | 1/2016 | Lee et al. | |
| 2016/0081959 A1 | 3/2016 | Bartos et al. | |
| 2016/0263135 A1 | 9/2016 | Komorowski et al. | |
| 2017/0135969 A1 | 5/2017 | Komorowski | |
| 2017/0348235 A1 | 12/2017 | White | |
| 2018/0071264 A1 | 3/2018 | Nelson et al. | |
| 2020/0078394 A1 | 3/2020 | Komorowski | |
| 2020/0155510 A1 | 5/2020 | Komorowski | |
| 2021/0100776 A1 | 4/2021 | Nelson et al. | |
| 2022/0265704 A1 | 8/2022 | Komorowski | |

FOREIGN PATENT DOCUMENTS

| | | |
|---|---|---|
| EP | 1911357 A1 | 4/2008 |
| EP | 2805730 A1 | 11/2014 |
| FR | 2610522 A1 | 8/1988 |
| FR | 2745498 A1 | 9/1997 |
| JP | S60094949 A | 5/1985 |
| JP | S6125688 B2 | 6/1986 |
| JP | S61282386 A | 12/1986 |
| JP | H04 169528 A | 6/1992 |
| JP | 2001181211 A | 7/2001 |
| JP | 2007503407 A | 2/2007 |
| JP | 2013529623 A | 7/2013 |
| JP | 2015522630 A | 8/2015 |
| MX | 2019011848 A | 3/2021 |
| WO | WO-1998/34647 A1 | 8/1998 |
| WO | WO-2000/45651 A1 | 8/2000 |
| WO | WO-2002/28379 A2 | 4/2002 |
| WO | WO-2004/017913 A2 | 3/2004 |
| WO | WO-2007/13655 A1 | 2/2007 |
| WO | WO-2011/161421 A1 | 12/2011 |
| WO | WO-2012/173808 A1 | 12/2012 |
| WO | WO-2014/016003 A1 | 1/2014 |
| WO | WO-2017/004226 A1 | 1/2017 |
| WO | WO-2018/045244 A1 | 3/2018 |
| WO | WO-2018/076108 A1 | 5/2018 |
| WO | WO-2020/051428 A1 | 3/2020 |

(56) References Cited

FOREIGN PATENT DOCUMENTS

| WO | WO-2020/102203 A1 | 5/2020 |
|---|---|---|
| WO | WO-2023/164272 A1 | 8/2023 |

OTHER PUBLICATIONS

Adams et al., "Nutritional and metabolic status of children with autism vs. neurotypical children, and the association with autism severity," Nutrition & Metabolism, 2011; 8(34): pp. 1-32.

Ahmad et al., "Treatment of Pyruvate Carboxylase Deficiency With High Doses of Citrate and Aspartate" American Journal of Medical Genetics, vol. 87, pp. 331-338 (1999).

Al-Owain et al., "Autism Spectrum Disorder in a Child with Propionic Acidemia" JIMD Reports, vol. 7, pp. 63-66 (2012).

Al-Qazzaz et al.; "Cognitive impairment and memory dysfunction after a stroke diagnosis: a post-stroke memory assessment," Neuropsychiatric Disease and Treatment, 2014; 10 : 1677-1691.

Allen et al. Ansel's Pharmaceutical Dosage Forms and Drug Delivery Systems, 8th Edition, eds., Lippincott Williams & Wilkins, Philadelphia, PA, 2005.

Asai et al., "Topical application of ex vivo expanded endothelial progenitor cells promotes vascularization and wound healing in diabetic mice," International Wound Journal, 2012: pp. 527-533.

Ask the dentist, how often should I go to the dentist for a teeth cleaning? [online], [retrieved Jul. 21, 2018]. Retrieved from the Internet: <URL: https://askthedentist.com/how-often-should-i-go-to-the-dentist-for-a-teeth-cleaning/>.

Bassler, "Hard water, food fibre, and silicon," British Medical Journal, 1978; 1 : p. 919.

Berge et al. "Pharmaceutical Salts" Journal of Pharmaceutical Sciences, 1977, vol. 66, No. 1, pp. 1-18.

Biotin sodium salt: retrieved from: <https://pubchem.ncbi.nlm.nih.gov/compound/Biotin-sodium-salt> Create Date Sep. 10, 2008 (Retrieved on Aug. 19, 2020).

Biotinate: retrieved from: <https://pubchem.ncbi.nlm.nih.gov/compound/Biotinate> Create Date May 23, 2006 (Retrieved on Aug. 19, 2020).

Blum et al., "Toxicologic evaluation of a novel, highly soluble biotin salt, magnesium biotinate" Food and Chemical Toxicology, vol. 153: p. 112267 (2021).

Bonnefont-Rousselot, "Glucose and reactive oxygen species," Curr. Opin. Clin. Nutr. Metab.Care, 2002; 5: pp. 561-568.

Calles-Escandon et al., "Diabetes and endothelial dysfunction: A clinical perspective." Endocrine Reviews, 2001; 22(1): pp. 36-52.

Calver et al., "Effect of local intra-arterial NG-monomethyl-L-arginine in patients with hypertension: the nitric oxide dilator mechanism appears abnormal," J. of Hypertension, 1992; 10: pp. 1025-1031.

Carboy et al. "Disease-modifying therapies for multiple sclerosis" Current Treatment Options in Neurology, 2003, vol. 5, pp. 35-54.

Carlisle, "In vivo Requirement for Silicon in Articular Cartilage and Connective Tissue Formation in the Chick," J. Nutr., 1976; 106: pp. 478-484.

Carlisle, "Silicon: An Essential Element for the Chick," Science, 1972; 178: pp. 619-621.

Carlisle, E.M. (1980) "Biochemical and morphological change associated with long bone abnormalities in silicon deficiency". J. Nutr. 110: 1046-1055.

Carlisle, et al. (1980) "A silicon requirement for normal growth of cartilage in culture." Fed. Proc. 39:787.

Carlson et al.; "Predictors of neurocognitive outcomes on antiretroviral therapy after cryptococcal meningitis: a prospective cohort study," 2014; Metabolic brain disease vol. 29, No. 2, pp. 269-279. (Year: 2014).

Chen et al., 1991, L-Arginine Abrogates Salt-sensitive Hypertension in Dahl/Rapp Rats, J. Clin. Invest. 88: 1559-1567.

Cherian et al., "L-arginine and Free Radical Scavengers Increase Cerebral Blood Flow and Brain Tissue Nitric Oxide Concentrations after Controlled Cortical Impact Injury in Rats," J. of Neurotrauma, 2003; 20(1): pp. 77-85.

Cicek et al., "The Protective Effects of a Combination of an Arginine Silicate Complex and Magnesium Biotinate Against UV-Induced Skin Damage in Rats" Frontiers in Pharmacology, vol. 12, Article 657207 (2021).

Clarkson et al., 1996, Oral L-Arginine Improves Endothelium-dependent Dilation in Hypercholesterolemic Young Adults, J. Clin. Invest. 97(8): 1989-1994.

Clowes et al., 1977, Suppression by heparin of smooth muscle cell proliferation in injured arteries Nature 265: 625-626.

Cooke et al., 1994, "Is NO an Endogenous Antiatherogenic Molecule," Arteriosclerosis and Thrombosis 14(5): 653-655.

Cosgrove, "Nitric Oxide Ingredients for Sports," Nutritional Outlook, [online], Nov. 8, 2013. Retrieved from the Internet: <URL: http://www.nutritionaloutlook.com/heart-health/nitricoxide-ingredients-sports>.

Creager et al., 1992, "L-Arginine Improves Endothelium-dependent Vasodilation in Hypercholesterolemic," Humans J. Clin. Invest. 90:1248-1253.

Curtis, et al., "Nitric oxide supplementation of synthesis of block-which is the better approach to treatment of heart disease?", Trends in Pharmacological Sciences, 18(7):239-244 (1997).

Deans, "Targeted Diet Interventions in Autistic Spectrum Disorders," [online], 2014, pp. 1-2, [retrieved on Feb. 16, 2021 ]. Retrieved from the Internet: <URL: https://www.psychologytoday.com/sg/blog/evolutionary-psychiatry/201402/targeted-diet-interventions-in-autistic-spectrum-disorders-0>.

Demir et al., "Effects of a Combination of Arginine Silicate Inositol Complex and a Novel Form of Biotin on Hair and Nail Growth in a Rodent Model" Biological Trace Element Research, 201:751-765 (2023).

Drexler et al., 1991, "Correction of endothelial dysfunction in coronary microcirculation of hypercholesterolaemic patients by L-arginine," Lancet 338:1546-1550.

Durmas et al., "Arginine Silicate Inositol Complex Accelerates Cutaneous Wound Healing" Biological Trace Element Research, 177: 122-131 (2017).

Edelman et al., "Effect of controlled adventitial heparin delivery on smooth muscle cell proliferation followina endothelial iniury," Proc. Natl. Acad. Sci. USA, 1990; 87: pp. 3773-3777.

Edmonds et al.; "Water consumption, not expectancies about water consumption, affects cognitive performance in adults," Elsevier, Appetite, 2013; 60: pp. 148-153.

Eisinger et al. (1993) "Effects of silicon, fluoride, etidronate and magnesium on bone mineral density: a retrospective study." Magnisium Research. 6(3):247-249.

Garson et al., "Organosilicon Entities as Prophylactic and Therapeutic Agents," J. of Pharmaceutical Sciences, 1971; 60(8): pp. 1113-1127.

Geoffrey Stark, DDS, How much toothpaste per brushing is recommended? [online], [retrieved Jul. 23, 2018]. Retrieved from the Internet: <URL: https://secure.advantagedental.com/images/files/faq_toothpaste.htm>.

Goodman and Gilman's: The Pharmacological Basis of Therapeutics, 8th Ed., Gilman et al., eds., Pergamon Press, Elmsford, NY, 1990.

Greenhalgh et al., "PDGF and FGF stimulate wound healing in the genetically diabetic mouse," American Journal of Patholoay, 1990; 136(6):1235-1246.

Guyton et al., "Inhibition of rat arterial smooth muscle cell proliferation by heparin," Gire. Res., 1980; 46: pp. 625-634.

Hoogman et al.; "Cognitive outcome in adults after bacterial meningitis," Journal of Neurology, D Neurosurgery & Psychiatry, 2007; 78(10): pp. 1092-1096.

Hott et al., "Short-term effects of organic silicon on trabecular bone in mature ovariectomized rats," Calcif. Tissue Int., 1993; 53: pp. 174-179.

Hung et al.; "Cognitive Decline among Patients with Chronic Obstructive Pulmonary Disease," American Journal of Respiratory and Critical Care Medicine, 2009; 180(2): pp. 134-137.

Im-Emsap et al., Chapter 9: Disperse Systems, in Modern Pharmaceutics, 4th Edition, Banker et al., eds., Marcel Dekker, Inc., New York NY, 2002: pp. 237-285.

(56) References Cited

OTHER PUBLICATIONS

International Search Report and Written Opinion dated Aug. 26, 2016 in PCT/US16/040128.
International Search Report and Written Opinion dated Jan. 27, 2020 in PCT/US19/58653.
International Search Report and Written Opinion dated Mar. 8, 2021 in PCT/US20/65418.
International Search Report and Written Opinion for International Application No. PCT/US2023/014077 dated May 23, 2023.
International Search Report and Written Opinion for PCT/US2017/049757, mailed Nov. 7, 2017.
International Search Report and Written Opinion issued in connection with PCT/US2019/049915, mailed Nov. 12, 2019.
International Search Report and Written Opinion issued in PCT/US2019/060932, mailed Jan. 29, 2020.
Isselbacher et al., "Harrison's Principles of Internal Medicine", 13th edition, vol. 2, (eds.), published 1994 by McGraw-Hill in 1994, p. 1321.
Kalman et al., "A Randomized Double-Blind Evaluation of a Novel Biotin and Silicon Ingredient Complex on the Hair and Skin of Healthy Women" Journal of Clinical & Experimental Dermatology Research, vol. 12, issue 1, No. 551 (2021).
Kelly et al., "Insulin resistance: lifestyle and nutritional interventions," Alternative Medicine Review, 2000; 5(2): pp. 109-132.
Kelly et al., "L-Theanine and Caffeine in Combination Affect Human Cognition as Evidenced by Oscillatory alpha-Band Activity and Attention Task Performance," J. Nutr., 2008; 138(8): pp. 1572S-1577S.
Khaibullin et al., "Elevated Levels of Proinflammatory Cytokines in Cerebrospinal Fluid of Multiple Sclerosis Patients," May 18, 2017 (May 18, 2017), Front. Immunol., 2017; 8(531): pp. 1-10.
Kirkorian et al.; "Improved cognitive-cerebral function in older adults with chromium supplementation," Nutritional Neuroscience, 2010; 13(3): pp. 116-122.
Komorowsky et al., "The effect of combination of an Arginine Silicate Complex and Magnesium Biotinate on hair and nail growth in rats (PO6-026-19)", Curr Dev Nutr 3.Suppl 1 (2019).
Kottke et al., Chapter 10: Tablet Dosage Forms, in Modern Pharmaceutics, 4th Edition, Banker et al., eds., Marcel Dekker, Inc., New York NY, 2002: pp. 287-333.
Kumar et al.; "Promising Therapeutics with Natural Bioactive Compounds for Improved Learning and Memory—A Review of Randomized Trials," 2012, Molecules, vol. 17, pp. 10503-10539. (Year: 2012).
Kurmann et al.; "Progressive multifocal leukoencephalopathy in common variable immunodeficiency: mitigated course under mirtazapine and mefloquine," 2015; Journal of neurovirology, vol. 21, No. 6, pp. 694-701. (Year: 2015).
Laurant et al., "Dietary L-Arginine Attenuates Blood Pressure in Mineralocorticoid-Salt Hypertensive Rats," Clin. and Exper. Hypertension, 1995; 17(7): pp. 1009-1024.
Lieberman et al., Pharmaceutical Dosage Forms: Tablets, eds., Marcel Dekker, Inc., New York, NY, 1989.
Lockhart et al.; "Cognition enhancing or neuroprotective compounds for the treatment of cognitive disorders: why? when? which?" 2003, Elsevier; Experimental Gerontology, vol. 38, pp. 1119-1128. (Year: 2003).
Loeper et al., "The Antiatheromatous Action of Silicon," Atherosclerosis, 1979; 33: pp. 397-408.
Loeper et al., "The Physiological Role of the Silicon and its Antiatheromatous Action, in Biochemistry of Silicon and Related Problems," Bendz G et al. Eds. Plenum Press, NY, 1978; pp. 281-296.
Loscher, "Endothelium-derived nitric oxide: The endogenous nitrovasodilator in the human cardiovascular system," Eur. Heart J., 1991; 12(Suppl. E): pp. 2-11.
Machine translation of DE20315174 (U1), published Nov. 12, 2003.
Machine translation of EP1040815 (A1), published Oct. 4, 2000.

Marsh et al., "Relationships Among Balance, Visual Search, and Lacrosse-Shot Accuracy," J Strength Cond Res, 2010; 24(6): DD. 1507-1514.
Maulik et al., "Nitric Oxide signaling in ischemic heart," Cardiovasc. Res., 1995; 30(4): pp. 593-601.
McPherson et al., "Superoxide activates constitutive nitric oxide synthase in a brain particulate fraction," Biochemical and Biophysical Research Communications, 2002; 296: pp. 413-418.
Miller et al., "Practical Clinical Application of Biochemical Markers of Bone Turnover," Journal of Clinical Densitometry, 1999; 2(3): pp. 323-342.
Mind Lab Pro®, "Nootropics for Ganiers—Level Up Your Ganiing \Nith Cognitive Enhancers," Nootropics for Gamers—Level Up Your Gaming with Cognitive Enhancers, 2018, [online], [retrieved on Dec. 18, 2019]. Retrieved from the Internet: <URL: https://www.mindlabpro.com/blogs/nootropics/nootropics-gamers-gaming>.
Mirmiran et al., "Dietary L-arginine intakes and the risk of metabolic syndrome: a 6-year follow-up in tehran lipid and glucose study", *Preventive Nutrition and Food Science* 22(4): 263 (2017).
Modern Biotechnology: vol. 2, Editors-in-Chief Chu Ju and Li Yourong.—Shanghai: East China University of Science and Technology Press, Mar. 2008: pp. 293-294.
Moncada et al., "The L-Arginine-Nitric Oxide Pathway," The New. Engl. J. of Med., 1993; 329(27): pp. 2002-2012.
Nitric Oxide Benefits, Supplements, Sources, and Side Effects, [online], [dated May 24, 2015]. Retrieved from the Internet: <URL:https://web.archive.org/web/20150524100645/http://www.nitricoxide.org:80/>.
Nitrosigine Launch, [online], [dated May 16, 2013]. Retrieved from the Internet: <URL: https://nutrition21.com/2013/05/nutrition21-launches-nitrosigine-a-novel-patented-source-of-inositol-stabilized-arginine-silicate/>.
Nutrition 21, Inc., EurekAlert!, [online], public release Dec. 13, 2007. Retrieved from the Internet: <URL: httDs://www.eurekalert.ora/Dub releases/2007-12/n2-ncd121207.DhD>.
Ojalvo et al., "Pharmacokinetics of a Novel Form of Biotin, Magnesium Biotinate, in Healthy Subjects (P06-027-19)", Current Developments in Nutrition, 2019; vol. 3(1): p. 537.
Ojalvo et al., "The Safety and Absorption of Magnesium Biotinate in Rats (P06-029-19)", Current Developments in Nutrition, 2019; 3(1): p. 539.
Otani, JP 2004099599 A, Apr. 2, 2004, machine translation. (Year: 2004).
Parr, "Silicon, Wine, and the Heart," Lancet, 1980; p. 1087.
Partial European Search Report for European Application No. 03793307.4, dated Aug. 2, 2007.
Pharmaceutics, Editors-in-Chief: Chen Weiwei, et al.—Xi'an Jiaotong University Press. Dec. 2013: pp. 6-8.
Pourabdolhossein et al., "Nogo Receptor Inhibition Enhances Functional Recovery following Lysolecithin-Induced Demyelination in Mouse Optic Chiasm," Plos One, 2014; 9(9): pp. 1-13.
Prescha et al., "Dietary silicon and its impact on plasma silicon levels in the Polish population", *Nutrients* 11(5): 980 (2019).
Proctor et al., "Metabolic effects of a novel silicate inositol complex of the nitric oxide precursor arginine in the obese insulin-resistant JCR:LA-cp rat," Metabolism Clinical and Experimental, 2007; 56: pp. 1318-1325.
Proctor et al., "A novel complex of arginine-silicate improved micro and macrovascular function and inhibits glomerular sclerosis in insulin-resistant JCR:LA-cp rats," Diabetologia, 2005; 48(9): pp. 1925-1932.
Quick Reference Guide for Drugs Used for Skin Diseases, Editor-in-Chief, Mao Wei'an.—Beijing: Jindun Publishing House, Apr. 2014; p. 316.
Rood-Ojalvo et al., "The benefits of inositol-stabilized arginine silicate as a workout Ingredient," Journal of the International Society of Sports Nutrition, 2015; 12(suppl. 1): p. 14.
Roth et al., "Prenatal Administration of Biotin in Biotin Responsive Multiple Carboxylase Deficiency" Pediatric Research, vol. 16, pp. 126-129 (1982).

(56) References Cited

OTHER PUBLICATIONS

Rubanyi, "Endothelium-Derived Vasoactive Factors in Health and Disease, in Cardiovascular Significance of Endothelium-Derived Vasoactive Factors," Rubanyi, G.M., ed., Futura Publishing Company, Inc., NY xi-xix, 1991.

Sahin et al., "Effects of magnesium biotinate supplementation on serum insulin, glucose and lipid parameters along with liver protein levels of lipid metabolism in rats" Magnesium Research, 23(1): 9-19 (2021).

Salt metathesis reaction, Wikipedia [online], [retrieved 2018]. Retrieved from the Internet: <URL: https://en.wikipedia.org/wiki/Salt_metathesis_reaction>.

Saul, [online], [retrieved on Nov. 27, 2017]. Retrieved from the Internet: <URL: <http://www.doctoryourself.com/fatigue.html>, 2005.

Schiffman et al., "Taste of nutrients: amino acids, vitamins and fatty acids," Perception & Psyschophysics, 1975; 17(2): pp. 140-146.

Schwarz et al., "Growth-promoting effects of silicon in rats," Nature, 1972; 239: pp. 333-334.

Schwarz et al., "Inverse Relation of Silicon in Drinking Water and Atherosclerosis in Finland," Lancet, 1977; pp. 538-539.

Schwarz, "Significance and Functions of Silicon in Warm-Blooded Animals, in Biochemistry of Silicon and Related Problems," Bendz, G et al., Eds., Plenum Press, NY 207-230 (1978).

Schwarz, "Silicon, Fibre, and Atherosclerosis," Lancet, 1977; pp. 454-457.

Serajuddin, "Salt formation to improve drug solubility", Advanced drug delivery reviews 59.7 (2007): 603-616.

Seymour, "The effect of cutting upon the rate of hair growth", American Journal of Physiology—Legacy Content 78(2): 281-286 (1926).

Simons et al., "Can psychiatric childhood disorders be due to inborn errors of metabolism?" Eur Child Adolesc Psychiatry, 2017; 26: pp. 143-154.

Spilioti et al., "Evidence for treatable inborn errors of metabolism in a cohort of 187 Greek patients with autism spectrum disorder (ASD)," Frontiers in Human Neuroscience, 2013; 7(858): pp. 1-7.

Su et al., "Experimental Measurement and Modeling of the Solubility of Biotin in Six Pure Solvents at Temperatures from 298.15 K to 333.85 K," J. Chem. Eng. Data, 2014; 59: pp. 3894-3899.

Supplementary European Search Report for European Application No. EP 03793307.4 dated Dec. 4, 2008.

Supplementary European Search Report issued in EP 17847596 dated Mar. 17, 2020.

Svehla, "Reaction of Silicates," Vogels Textbook of Macro and Semimicro Qualitative Inorganic Analysis 5th Edition, Lonaman, London, 1979; pp. 350-353.

Sylla et al., "An Open-label Experience Trial to Evaluate the Effects of a Novel Supplement and Hair Serum Combination on Hair Skin and Nails in Healthy Women" Current Developments in Nutrition, vol. 5, Issue Supplement 2, p. 374 (2021).

Toker et al., "The effects of hydrogen sulphide on alveolar bone loss in periodontitis," Minerva Stomatol, 2014; 63(4): pp. 103-110.

Tourbah et al., "MD1003 (high-dose biotin) for the treatment of progressive multiple sclerosis: A randomised, double-blind, placebo-controlled study," Multiple Sclerosis Journal, 2016; 22(13): pp. 1719-1731.

Tsao et al., "Enhanced endothelial adhesiveness in hypercholesterolemia is attenuated by L-arginine," Circulation, 1994; 89(5): pp. 2176-2182.

U.S. Department of Health and Human Services, FDA, "Guidance for Industry: Q3C Impurities: Residual Solvents," Dec. 1997.

University of California—Davis Health System. "Children with autism have mitochondrial dysfunction, study finds." ScienceDaily, Nov. 30, 2010 [retrieved on Oct. 18, 2019]. Retrieved from the Interne<https://www.sciencedaily.com/releases/2010/11/101130161521.htm>.

Van Lente, "Markers of inflammation as predictors in cardiovascular disease," Clinica Chimica Acta., 2000; 293: pp. 31-52.

Wang et al. "Effects of nitric oxide synthase inhibitors on systemic hypotension, cytokines and inducible nitric oxide synthase expression and lung injury following indotoxin administration in rats," J. Biomed. Sci., 1999; 6: pp. 28-35.

Wang et al., "Spatial Memory Impairment is Associated with Hippocampal Insulin Signals in Ovariectomized Rats," PLOS One, 2014; 9(8): pp. 1-7.

Wikipedia, "Clinically isolated syndrome," Jul. 17, 2018, [online]. Retrieved on Jan. 8, 2020 from <https://en.wikipedia.org/wiki/Clinically_isolated_syndrome>.

Wikipedia, "Multiple sclerosis", Jul. 26, 2018, [online]. Retrieved on Jan. 8, 2020 from <https://en.wikipedia.org/wiki/Multiple_sclerosis>.

Wilson et al., "Impaired cognitive function and mental performance in mild dehydration," European Journal of Clinical Nutrition, 2003; 57(2): pp. S24-S29.

Wu Mao-ying et al., "New Technology for Synthesis of Magnesium Stearate," Science & Technology in Chemical Industry, 2000; 8(6): pp. 43-45. (English translation provided.).

Zaffanello et al., "A Case of Partial Biotinidase Deficiency Associated With Autism," Child Neuropsychology, 9(3):184-188 (2010).

Zempleni et al., "Biotin biochemistry and human requirements," The Journal of Nutritional Biochemistry, 1999; 10: p. 128-138.

FIG. 5

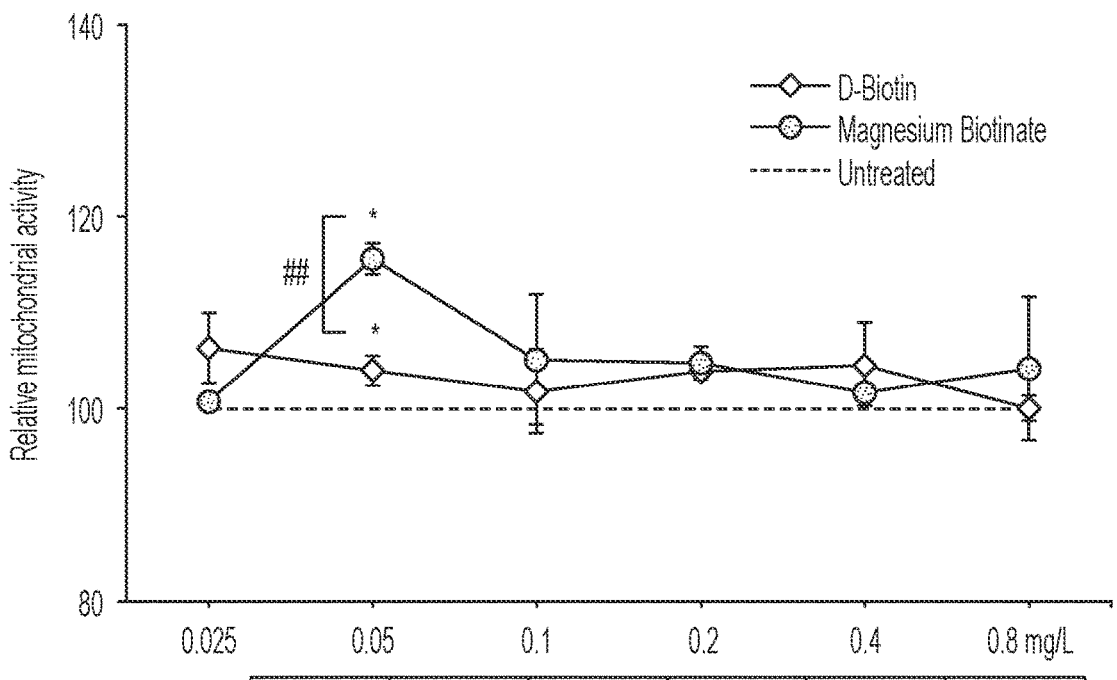

Cellular energy production of PBMC in 24-hour cultures. PBMC were exposed to serial dilutions of products for 24 hours after which time cultures were processed in the colorimetric MTT assay. Results reflect the sum of the metabolic activity of the cells in each culture. The colorimetric readings are shown as the average ± standard deviation each triplicate set of cell cultures, compared to untreated cultures (horizontal grey line). Statistical significance for within treatment analysis is indicated by *, $P<0.05$ while statistical significance for between treatments is indicated by ##, $P<0.01$.

MAGNESIUM BIOTINATE COMPOSITIONS AND METHODS OF USE

CROSS-REFERENCE TO RELATED APPLICATIONS

This application is a continuation of U.S. application Ser. No. 16/855,966, filed Apr. 22, 2020; which is a divisional of U.S. application Ser. No. 15/693,223 filed Aug. 31, 2017, which claims benefit of U.S. Provisional Application No. 62/382,438, filed Sep. 1, 2016, the contents of each of which is incorporated by reference herein in their entirety.

BACKGROUND

Field

The present application relates to magnesium biotinate compositions and methods of use. The methods and compositions disclosed herein are particularly useful for providing bioavailable biotin to mammals and treating or preventing symptoms of biotin deficiency.

Description of the Related Art

Biotin is an essential water-soluble vitamin also known as Vitamin H, Coenzyme R, and Vitamin B7. It is an essential co-factor for five known carboxylases involved in fatty acid biosynthesis, gluconeogenesis, branched-chain amino acid metabolism, fatty acid metabolism, tricarboxylic acid cycle anaplerosis, and pleiotropic gene regulation, particularly for genes in carbohydrate metabolism. Biotin has Chemical Abstracts Service Registry No. 58-85-5 and the general formula:

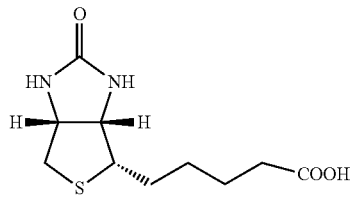

Biotin plays key roles in a variety of metabolic reactions and is essential for normal mammalian growth, development, and health. For example, studies suggest a role for biotin in multiple cellular processes, including colonocyte nutrition, histone modification, cell proliferation, DNA repair, protein expression (including insulin receptor, glucokinase, certain oncogenes, holocarboxylase synthetase, and sodium-multivitamin transporter (hSMVT)), and immune functions, including production of antibodies, macrophage function, and differentiation of T and B lymphocytes. Biotin also plays a role in suppression of hepatic phosphoenolpyruvate carboxykinase, a key enzyme in gluconeogenesis. Accordingly, serious clinical abnormalities occur in biotin-deficient individuals, including, among other effects, growth retardation, neurological disorders, and dermatological disorders.

Biotin is not synthesized by mammals but is supplied through dietary sources and from gut microflora, but natural mechanisms may be inadequate to supply sufficient quantities of biotin and synthetic supplementation may also be inadequate. Biotin is absorbed from the gastrointestinal tract by sodium-dependent vitamin transporters (SMVT) and non-specific monocarboxylate transporters.

Biotin deficiency frequently occurs during pregnancy, in subjects with abnormal metabolism, in subjects on long-term therapy with anticonvulsant agents, in subjects on long-term use of parenteral nutrition, in alcoholics, in subjects with inflammatory bowel disorders, and in subjects with seboric dermatitis and Lenier's disease. Genetic disorders such as biotinidase deficiency or holocarboxylase synthetase deficiency may result in biotin deficiency.

Such deficiencies are typically responsive to the administration of biotin. The recommended daily allowance for biotin has not been established but is estimated to be 35 micrograms (μg) and 150-300 μg for infants and adults, respectively. Pharmacological doses of 5-10 milligrams (mg)/kg body weight/day are well tolerated and generally relieve severe and/or genetically related biotin deficiencies. In recent clinical studies, daily doses as high as 300 mg biotin have been evaluated for treatment of disabling neurological conditions such as progressive multiple sclerosis.

However, the ability to reliably and consistently provide exogenous biotin to subjects is severely restricted by its low solubility in water (about 22 mg biotin/100 mL) and other pharmaceutically acceptable solvents. This low solubility corresponds to low, and unpredictable, bioavailability, making consistent and reliable biotin delivery challenging, and at times impossible, through the natural diet and existing supplementation regimens. For example, biotin may be administered with a cyclodextrin, and dissolved in a small amount of aqueous ammonia (EP 056902 and U.S. Pat. No. 5,840,881). Biotin may also be provided in a composition with lactose or an amino acid, or as an alkalolamine salt (U.S. Pat. Nos. 4,277,488; 4,725,427; and 5,550,249), or as an ester or amide biotin prodrug (U.S. Patent Application Publication No. 2014/0011255).

Thus, there is a long-standing and unmet need for biotin compositions to provide enhanced solubility and bioavailability, to facilitate consistent reliable delivery of therapeutic quantities of biotin.

SUMMARY OF THE INVENTION

Some embodiments relate to nutritional and therapeutic compositions that are useful for enhancing the solubility of D-biotin in water and other aqueous solutions. Such nutritional and therapeutic compositions do not occur naturally and are markedly different than naturally occurring compositions of biotin. Methods disclosed herein include enhancing the water-solubility of D-biotin by providing D-biotin as magnesium D-biotinate compositions. Methods for enhancing the bioavailability of D-biotin are also disclosed and may comprise administering to a subject a safe and effective amount of a magnesium D-biotinate composition. Further, a method of enhancing the bioavailability of D-biotin in warm-blooded animals is disclosed. Such a method may comprise administering a therapeutically effective amount of a composition comprising a magnesium D-biotinate composition. Method can comprise providing a nutritional and/or therapeutic, water-soluble magnesium D-biotinate composition for enhancing the bioavailability of D-biotin. The composition is useful, for example, in mammals. Some embodiments comprise a composition comprising magnesium biotinate wherein the composition comprises less than or equal to about 0.8% sodium by weight compared to the weight of the total composition. Some embodiments comprise a composition comprising magnesium biotinate wherein the composition comprises less than or equal to about 0.8% sodium by weight compared to the weight of the magnesium biotinate. Some embodiments provide for a composition comprising magnesium biotinate wherein the magnesium biotinate has a solubility of at least about 10 g per liter of water. In some embodiments, the solubility of a magnesium biotinate composition may be between about 22 mg per 100 ml of water and about 1,000 mg per 100 mL of water. In some embodiments, the solubility of a magnesium biotinate composition may be between about 50 mg per 100 mL of water and about 1,000 mg per 100 ml of water. In some embodiments, the solubility of a magnesium biotinate composition may be between about 75 mg per 100 ml of water and about 1,000 mg per 100 mL of water. Compositions as described herein may have improved absorption compared to D-biotin. Some embodiments of compositions described herein may not contain any magnesium in the composition. Some embodiments of compositions described herein may not contain any biotin, and more particularly, any D-biotin.

In some aspects, the compositions disclosed herein may be used to treat or prevent biotin deficiencies. For example, the compositions may be administered to restore depleted biotin levels caused by the administration of one or more other drugs. The compositions may also be used to use treat or prevent, diseases such as multiple sclerosis and other diseases associated with defects in myelin sheaths and/or associated with nerve damage associated with demyelination. Other features, advantages, and embodiments of the invention will be apparent to those of ordinary skill in the art from the following description, examples, and appended claims.

Some embodiments provide a composition comprising an effective amount of magnesium biotinate and a pharmaceutically acceptable vehicle, carrier, or diluent. In some embodiments, the composition is a solid composition. In some embodiments, the composition comprises a sustained-release matrix. In some embodiments, the composition is enteric coated. In some embodiments, the composition comprises between about 10 µg to about 1,000 µg of magnesium biotinate. For example, some embodiments include about 50 µg or about 100 µg of magnesium biotinate. Some embodiments comprise about 300 µg of magnesium biotinate. Some embodiments comprise about 200 µg to about 400 µg of magnesium biotinate. Some embodiments include about 500 µg or about 750 µg of magnesium biotinate. Some embodiments may comprise between about 250 µg and about 350 µg, between about 275 µg and about 325 µg, between about 300 µg and about 400 µg, between about 400 µg and 500 µg, between about 450 µg and about 550 µg, between about 400 µg and 600 µg, between about 600 µg and about 800 µg, between about 650 µg and about 850 µg, between about 700 µg and about 1,000 µg, between about 250 µg and about 1,000 µg, between about 800 µg and about 1,100 µg, between about 900 µg and about 1,000 µg, between about 950 µg and about 1,050 µg, and ranges therebetween of magnesium biotinate. Some embodiments may comprise between about 250 mg and about 350 mg, between about 275 mg and about 325 mg, between about 300 mg and about 400 mg, between about 400 mg and 500 mg, between about 450 mg and about 550 mg, between about 400 mg and 600 mg, between about 600 mg and about 800 mg, between about 650 mg and about 850 mg, between about 700 mg and about 1,000 mg, between about 250 mg and about 1,000 mg, between about 800 mg and about 1,100 mg, between about 900 mg and about 1,000 mg, between about 950 mg and about 1,050 mg, between about 0.5 mg and 10,000 mg, between about 200 and about 10,000 mg, between about 300 mg and about 5,000 mg, between about 300 and about 10,000 mg, between about 1,000 mg and about 10,000 mg, between about 5,000 and about 10,000 mg, between about 1,000 mg and about 5,000 mg, between about 250 mg and about 3,000 mg, between about 500 mg and about 2,500 mg, between about 7,000 and about 10,000 mg and ranges therebetween and magnesium biotinate. In some embodiments, the composition may comprise at least about 200 µg, 300 µg, 400 µg, 500 µg, 1,000 µg, 10 mg, 100 mg, 300 mg, 500 mg, 700 mg, 1,000 mg, 3,000 mg, 5,000 mg, 7,000 mg, or 10,000 mg of magnesium biotinate, and ranges and limits therebetween.

Some embodiments provide a method of treating or preventing a disease, disorder, or condition associated with biotin deficiency in a mammal. Such mammals may be known to have or be at risk for developing biotin deficiency. Embodiments of methods of treating or preventing a disease, disorder, or condition can comprise administering an amount of magnesium biotinate effective to treat or prevent a disease, disorder, or condition associated with biotin deficiency in the mammal. In some embodiments, the disease, disorder, or condition, is selected from the group consisting of biotinidase deficiency, multiple carboxylase deficiency, and holocarboxylase synthetase deficiency, brittle hair, excessive hair loss, alopecia, anemia, one or more topical fungal infections, seborrheic dermatitis, hallucinations, lethargy, anorexia, depression, myalgia, paresthesia, excessive fatigue, somnolence, prolonged anticonvulsant therapy, prolong used of total parenteral nutrition, malnutrition, prolonged antibiotic therapy, hypotonia, pregnancy, short bowel syndrome, ketogenic dieting, excessive alcohol consumption, smoking, cystic fibrosis, or combinations of the foregoing. In some embodiments, the amount of magnesium biotinate administered is between about 10 µg to about 1,000 µg per day. In some embodiments, the magnesium biotinate is administered orally.

Some embodiments provide a method of improving skin texture comprising: identifying abnormal skin texture in a mammal; and administering a therapeutically effective amount of magnesium biotinate to the mammal. Some embodiments provide a method of improving skin texture comprising: administering a therapeutically effective amount of magnesium biotinate to the mammal to improve skin texture. In some embodiments, identifying can include administering a test that is sensitive to detecting one of the following: allergic reactions, stress-induced rash, eczema, acne vulgaris, acne rosacea, hives, seborrheic dermatitis, and psoriasis. In some embodiments, the testing includes a diagnosis of one or more of allergic reactions, stress-induced rash, eczema, acne vulgaris, acne rosacea, hives, seborrheic dermatitis, and psoriasis.

In some embodiments, the amount of magnesium biotinate administered is between about 10 µg to about 1,000 µg per day. In some embodiments, the magnesium biotinate is administered orally.

Some embodiments provide a method of treating or preventing a disease, disorder, or condition associated with nerve demyelination in a mammal. Such mammals may be known to have or be at risk for developing nerve demyelination. Methods of treating or preventing a disease, disorder, or condition associated with nerve demyelination in a mammal can comprise administering an amount of magnesium biotinate effective to treat or prevent a disease, disorder, or condition associated with nerve demyelination in the mammal. Some embodiments provide a method of maintaining healthy levels of biotin in a mammal comprising administering an effective amount of magnesium biotinate to the mammal. Some embodiments provide a method of maintaining optimum levels of biotin in a mammal comprising administering an effective amount of magnesium biotinate to the mammal. Some embodiments provide a method of promoting optimum levels of biotin in a mammal comprising administering an effective amount of magnesium biotinate to the mammal. Some embodiments provide a method of promoting healthy levels of biotin in a mammal comprising administering an effective amount of magnesium biotinate. Some embodiments provide methods of increasing bioavailability of biotin in a mammal comprising administering an effective amount of magnesium biotinate.

In some embodiments, the disease, disorder, or condition is selected from a demyelinating myelinoclastic disease, a demyelinating leukodystrophic disease, multiple scleroris, nerve damage, Devic's disease, Tabes dorsalis, central pontine myelinolysis, progressive multifocal leukoencephalopathy, Guillain-Barré syndrome, Charcot-Marie-Tooth disease, chronic inflammatory demyelinating polyneuropathy, copper deficiency, and progressive inflammatory neuropathy, or combinations of the foregoing.

In some embodiments, the amount of magnesium biotinate administered is between about 10 µg to about 1,000 µg per day. In some embodiments, the magnesium biotinate is administered orally.

Some embodiments provide a method of decreasing hair loss comprising: administering a therapeutically effective amount of magnesium biotinate to the mammal. Some embodiments of decreasing hair loss may comprise identifying hair loss in a mammal. In some embodiments, the identifying includes administering a test that is sensitive to detecting alopecia or stress-induced hair loss. In some embodiments, the testing includes a diagnosis of stress-induced hair loss.

In some embodiments, the amount of magnesium biotinate administered is between about 10 µg to about 1,000 µg per day. In some embodiments, the magnesium biotinate is administered orally.

Some embodiments provide a method of improving hair strength and texture comprising: administering a therapeutically effective amount of magnesium biotinate to the mammal. In some embodiments, a method of improving hair strength and/or texture can comprise identifying a mammal with abnormal hair strength and/or texture. Abnormal hair strength and texture may be indicated by, but not limited to, thin hair, brittle hair, rough hair, weak hair, and the like and such features of hair with abnormal hair strength would be readily envisaged and ascertainable by the skilled artisan in consideration of the present disclosure.

In some embodiments, identifying hair loss and/or identifying a mammal with abnormal hair strength and/or texture can comprise administering a scalp biopsy. In some embodiments, identifying can comprise a diagnosis of biotin deficiency. In some embodiments, the amount of magnesium biotinate administered can be between about 10 µg to about 1,000 µg per day. In some embodiments, the magnesium biotinate is administered orally.

Some embodiments provide a method of improving nail strength and texture comprising: administering a therapeutically effective amount of magnesium biotinate to the mammal. Some embodiments providing a method of improving nail strength can comprise identifying a mammal with abnormal nail strength and/or texture. In some embodiments, identifying a mammal with abnormal nail strength and/or texture can comprise administering a test that is sensitive to detecting biotin deficiency. In some embodiments, the testing includes a diagnosis of biotin deficiency.

In some embodiments, the amount of magnesium biotinate administered is between about 10 µg to about 1,000 µg per day. In some embodiments, the magnesium biotinate is administered orally. Examples of indications of abnormal nail strength and/or texture may include, but are not limited to, reduced ability to grow nails, slow nail growth, yellow-appearing nails, weak nails, nails that crack and/or break easily, and the like and such indications of abnormal nail strength and/or texture would be readily ascertainable and envisaged by the skilled artisan in consideration of the present disclosure. Certain embodiments provide a method of improving horse hoof strength and/or durability and some embodiments may provide a method for treating horse hoof injuries.

Some embodiments comprise methods of making magnesium D-Biotinate. The method may include adding D-biotin to a basic solution. The basic solution may be 1 N NaOH. The method may also include dissolving a magnesium salt into the sodium biotinate solution. The magnesium salt may be $MgCl_2$. The magnesium D-biotinate may be precipitated. In some aspects, acetone is added to cause precipitation. The precipitate may be washed with a solvent, dry filtered, and isolated. Some embodiments provide a method of making magnesium biotinate comprising the steps of: adding D-biotin to a basic solution to produce a sodium biotinate solution; dissolving a magnesium salt into the sodium biotinate solution; precipitating the magnesium D-biotinate; washing the precipitated magnesium D-biotinate with a solvent; and dry filtering the washed magnesium D-biotinate.

Some embodiments provide methods of increasing absorption of biotin and such a method may comprise administering an effective amount of magnesium biotinate to a mammal to increase the mammal's absorption of biotin. Some embodiments provide methods of increasing carboxylase activity and such a method may comprise administering an effective amount of magnesium biotinate to a mammal to increase carboxylase activity. For example, and without limitation, a method of increasing carboxylase activity may comprise increasing carboxylase activity wherein the carboxylase activity is selected from the activity of acetyl-CoA carboxylase ACC-1 and/or ACC-2, pyruvate carboxylase (PC), propionyl-CoA carboxylase (PCC), or methylcrotonyl-CoA carboxylase (MCC), and combinations thereof. Certain embodiments comprise methods of increasing cellular energy production comprising the steps of administering an effective amount of magnesium biotinate to a mammal to increase cellular energy production. Embodiments of the compositions as described herein may be used to increase a mammal's absorption of biotin, increase carboxylase activity, or increase cellular energy production, and combinations thereof.

BRIEF DESCRIPTION OF THE DRAWINGS

FIG. 4 shows the results of administration of biotin versus magnesium D-biotinate as disclosed herein.

FIG. 5 shows the results of administering D-biotin compared to administering magnesium biotinate in biotin-starved cell cultures.

DETAILED DESCRIPTION

Figure 1:
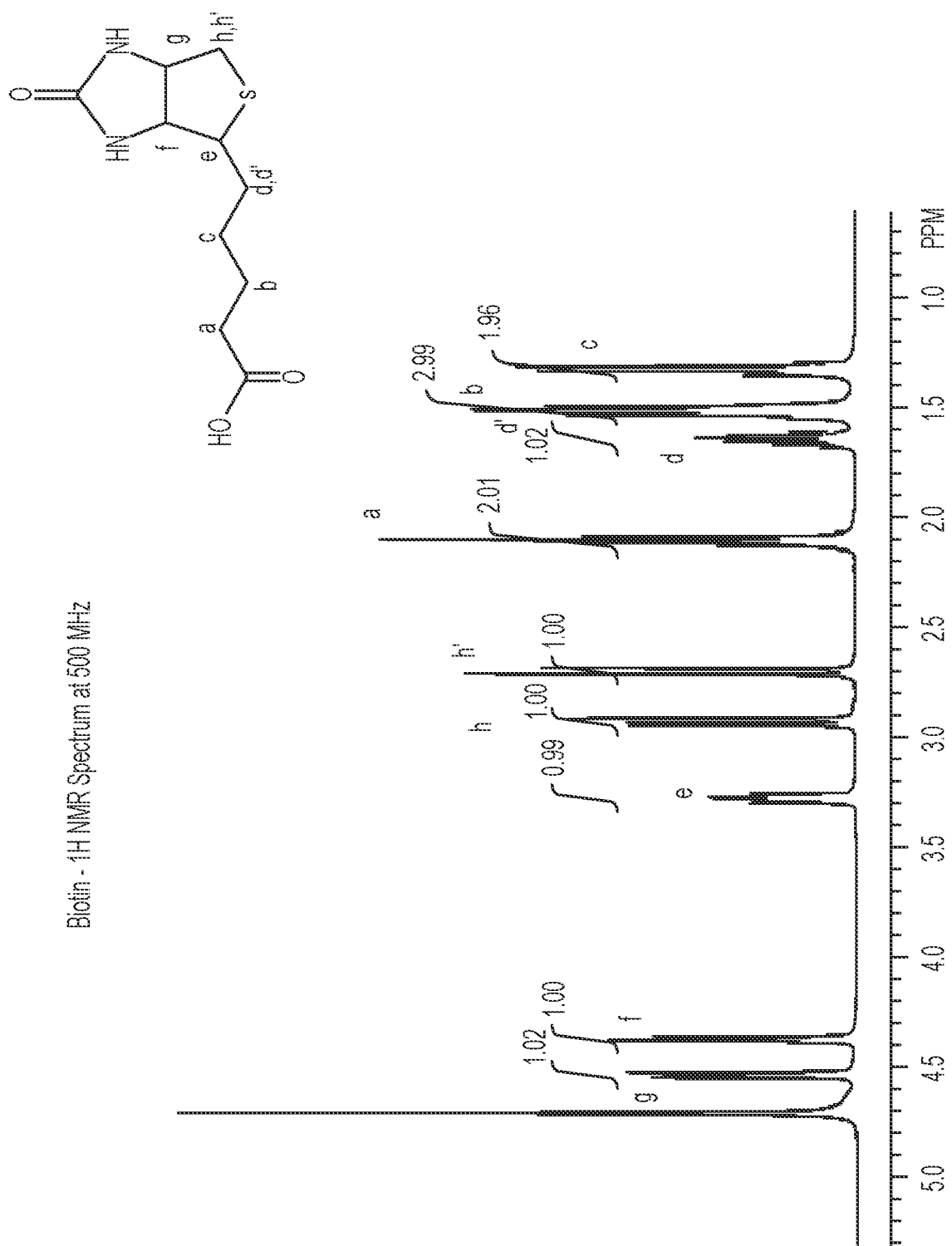
FIG. 1 depicts a $^1$H-NMR spectrum of D-biotin.

The terminology used in the description presented herein is not intended to be interpreted in any limited or restrictive manner, simply because it is being utilized in conjunction with a detailed description of certain specific embodiments described herein. Furthermore, embodiments described herein can include several novel features, no single one of which is solely responsible for its desirable attributes or which is essential to practicing the embodiments described herein.

As used herein, "identifying," refers to detecting or selecting a subject from a population of potential subjects, for example, to establish that a particular subject possesses certain properties or characteristics. "Identifying" may include, for example, self-identification, self-diagnosis, and diagnosis by a medical professional.

As used herein, "treat," "treatment," or "treating," refers to administering or providing a composition for prophylactic and/or therapeutic purposes.

As used herein, the terms "prophylactic treatment," "prevent," or "preventing," can refer to treating a subject who does not yet exhibit symptoms of a disease or condition, but who is susceptible to, or otherwise at risk of, a particular disease or condition, whereby the treatment reduces the likelihood that the patient will develop the disease or condition. A "disorder" is any condition that would benefit from treatment with the compositions described herein.

As used in the claims below and throughout this disclosure, the phrase "consisting essentially of" is meant including any elements listed after the phrase, and limited to other elements that do not interfere with or contribute to the activity or action specified in the disclosure for the listed elements. Thus, the phrase "consisting essentially of" indicates that the listed elements are required or mandatory, but that other elements are optional and can or cannot be present depending upon whether or not they affect the activity or action of the listed elements. For example, the use of a composition "consisting essentially of magnesium biotinate" for the treatment of a particular disease or disorder would exclude other ingredients that were known to be active in combating the particular disease or disorder.

As used herein, a composition that "substantially" comprises a compound means that the composition contains more than about 80% by weight, more preferably more than about 90% by weight, even more preferably more than about 95% by weight, and most preferably more than about 98% by weight of the compound.

The term "pharmaceutical formulation", "formulation", "composition" and the like can refer to preparations which are in such a form as to permit the biological activity of the active ingredients to be effective, and, therefore may be administered to a subject for therapeutic use along with dietary and/or nutritional supplement use. The meaning of these terms will be clear to the skilled artisan based upon the context in which they are used.

A "therapeutically effective amount" as used herein includes within its meaning a non-toxic but sufficient amount of a compound active ingredient or composition comprising the same for use in the embodiments disclosed herein to provide the desired therapeutic effect. Similarly "an amount effective to" or "an effective amount" as used herein includes within its meaning a non-toxic but sufficient amount of a compound active ingredient or composition comprising the same to provide the desired effect. The exact amount of the active ingredient disclosed herein required will vary from subject to subject depending on factors such as the species being treated, the age and general condition of the subject, the severity of the condition being treated, the particular agent being administered, the weight of the subject, and the mode of administration and so forth. Thus, it may not always be possible to specify an exact "effective amount." However, for any given case, an appropriate "effective amount" may be determined by one of ordinary skill in the art using only routine methods. In some aspects, a therapeutically effective amount may include a dosing regimen. For example, a therapeutically effective amount may include about 1 mg of magnesium biotinate orally consumed each day for fourteen consecutive days. In some aspects, a therapeutically effective amount may include about 1 mg of magnesium biotinate orally consumed each day for thirty consecutive days. Compositions including magnesium biotinate may include, for example, between 0.1-10 grams of magnesium biotinate.

In addition, the appropriate dosage of the compositions can depend, for example, on the condition to be treated, the severity and course of the condition, whether the composition is administered for preventive or therapeutic purposes, previous therapy, the patient's clinical history and response to the composition, the type of composition used, and the discretion of the attending physician. The composition can be suitably administered to the patient at one time or over a series of treatments and may be administered to the patient at any time from diagnosis onwards. The composition may be administered as the sole treatment or in conjunction with other drugs or therapies useful in treating the condition in question.

By way of example, a "therapeutically effective amount" and/or an "effective amount" of the compound disclosed herein can be, for example, 0.1 µg/kg, 0.5 µg/kg, 1 µg/kg, 1.5 µg/kg, 2.0 µg/kg, 2.5 µg/kg, 3.0 µg/kg, 3.5 µg/kg, 4.0 µg/kg, 4.5 µg/kg, 5.0 µg/kg, 10 µg/kg, 15 µg/kg, 20 µg/kg, 25 µg/kg, 30 µg/kg, 35 µg/kg, 40 µg/kg, 45 µg/kg, 50 µg/kg, 55 µg/kg, 60 µg/kg, 65 µg/kg, 70 µg/kg, 75 µg/kg, 80 µg/kg, 85 µg/kg, 90 µg/kg, 95 µg/kg, 100 µg/kg, 150 µg/kg, 200 µg/kg, 250 µg/kg, 300 µg/kg, 350 µg/kg, 400 µg/kg, 450 µg/kg, 500 µg/kg, 550 µg/kg, 600 µg/kg, 650 µg/kg, 700 µg/kg, 750 µg/kg, 80 µg/kg 0, 850 µg/kg, 900 µg/kg, 1 mg/kg, 1.5 mg·kg, 2.0 mg/kg, 2.5 mg/kg, 3 mg/kg, 3.5 mg/kg, 4.0 mg/kg, 4.5 mg/kg, 5 mg/kg, 5.5 mg/kg, 6 mg/kg, 6.5 mg/kg, 7 mg/kg, 7.5 mg/kg, 8 mg/kg, 8.5 mg/kg, 9 mg/kg, 9.5 mg/kg, 10 mg/kg 10.5 mg/kg, 11 mg/kg, 11.5 mg/kg, 12 mg/kg, 12.5 mg/kg, 13 mg/kg, 13.5 mg/kg, 14 mg/kg, 14.5 mg/kg, 15 mg/kg, 16 mg/kg, 17 mg/kg, 18 mg/kg, 19 mg/kg, 20 mg/kg, 21 mg/kg, 22 mg/kg, 23 mg/kg, 24 mg/kg, 25 mg/kg, 30 mg/kg, 35 mg/kg, 40 mg/kg, 45 mg/kg, 50 mg/kg, 55 mg/kg, 60 mg/kg, 65 mg/kg, 70 mg/kg, or more, or any fraction or integer in between any two of the preceding amounts of the compound. An effective amount may include any of the ranges and amounts discussed herein.

Accordingly, in some embodiments, the dose of the compound in compositions disclosed herein can be about 10 µg to about 10 g, preferably per day. For example, the amount of the complex can be 10 µg, 15 µg, 20 µg, 25 µg, 30 µg, 35 µg, 40 µg, 45 µg, 50 µg, 55 µg, 60 µg, 65 µg, 70 µg, 75 µg, 80 µg, 85 µg, 90 µg, 95 µg, 100 µg, 125 µg, 150 µg, 175 µg, 200 µg, 225 µg, 250 µg, 275 µg, 300 µg, 325 µg, 350 µg, 375 µg, 400 µg, 425 µg, 450 µg, 475 µg, 500 µg, 525 µg, 575 µg, 600 µg, 625 µg, 650 µg, 675 µg, 700 µg, 725 µg, 750 µg, 775 µg, 800 µg, 825 µg, 850 µg, 875 µg, 900 µg, 925 µg, 950 µg, 975 µg, 1000 µg, 1.25 g, 1.5 g, 1.75 g, 2.0 g, 2.25 g, 2.5 g, 2.75 g, 3.0 g, 3.25 g, 3.5 g, 3.5 g, 3.75 g, 4.0 g, 4.25 g, 4.5 g, 4.75 g, 5.0 g, 5.25 g, 5.5 g, 5.75 g, 6.0 g, 6.25 g, 6.5 g, 6.75 g, 7.0 g, 7.25 g, 7.5 g, 7.75 g, 8.0 g, 8.25 g, 8.5 g, 8.75 g, 9.0 g, 8.25 g, 9.5 g, 9.75 g, 10 g, or more, or any range or amount in between any two of the preceding values and any other ranges or amounts disclosed herein. The exemplary therapeutically effective amounts listed above, can, in some embodiments be administered in the methods described elsewhere herein on an hourly basis, e.g., every one, two, three, four, five, six, seven, eight, nine, ten, eleven, twelve, thirteen, fourteen, fifteen, sixteen, seventeen, eighteen, nineteen, twenty, twenty-one, twenty-two, twenty-three hours, or any interval in between, or on a daily basis, every two days, every three days, every four days, every five days, every six days, every week, every eight days, every nine days, every ten days, every two weeks, every month, or more or less frequently, as needed to achieve the desired therapeutic effect.

Some embodiments as described herein refer to "healthy levels" and/or "optimum levels" of biotin. In some embodiments, this specifically refers to the administration of D-biotinate as a nutritional or dietary supplement (which can be used interchangeably) and this administration achieves biotin increases in a mammal that cannot be achieved through a natural diet or natural food. For example and without limitation, administration of D-biotinate as described herein may allow a mammal with reduced levels of biotin to return to optimum or healthy levels, which is not achievable through a natural diet or through ingestion of natural food. In some embodiments, administration of D-biotinate as described herein can restore a mammal's biotin levels to healthy or optimum levels when the subject has depleted biotin levels resulting from conditions such as pregnancy. As described herein, the embodiments provide for unnatural supplementation that can overcome biotin deficiencies in mammals. In some embodiments, administration of D-biotinate as described herein can increase the bioavailability of biotin in a mammal, compared to the bioavailability of biotin from natural sources.

The present disclosure comprises nutritional and therapeutic compositions useful for enhancing the water solubility of biotin, and methods of using same. Some embodiments provide solid dosage forms of biotin. Some embodiments provide aqueous solutions of biotin. Some embodiments provide methods for increasing the water solubility of biotin comprising converting biotin to magnesium biotinate. Embodiments described herein comprising biotinate as a nutritional supplement can mean that the biotinate is present in an unnatural form, i.e., is presented in a supplement (e.g., in a pill or powder) that is different from that which occurs naturally, or the nutritional supplement results in unnatural supplementation that is unachievable through a non-supplemented diet.

The term "biotin" means D-biotin, an essential water-soluble vitamin also known as Vitamin H, Coenzyme R, or vitamin B7. D-Biotin has Chemical Abstracts Service Registry No. 58-85-5 and the general formula:

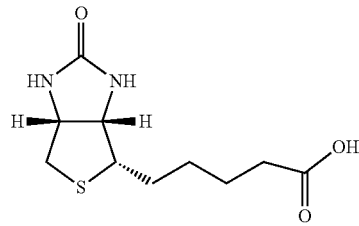

As used herein, the term "magnesium biotinate" refers to the magnesium salt of D-biotin, including magnesium hemi-biotinate. Magnesium D-biotinate is the magnesium salt of the carboxylic acid D-biotin, and does not occur naturally. In some embodiments, magnesium D-biotinate is a stable, non-hygroscopic, off-white powder having a defined composition, a molecular formula of $Mg(C_{10}H_{15}N_2O_3S)_2$ and a general formula of

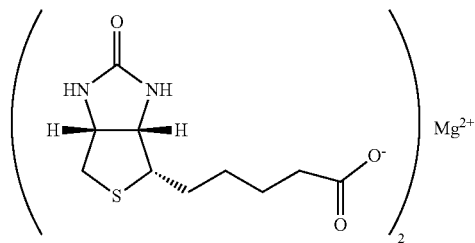

Some embodiments provide physiologically compatible magnesium biotinate hydrates, crystalline forms, polymorphic forms, solid forms having specific bulk densities or tap densities, and solid forms having specific particle sizes. Some embodiments provide compositions coated with pharmaceutically acceptable materials intended to modify its release and/or bioavailability, including, but not limited to Eudragit, microcrystalline cellulose, hydroxypropylmethylcellulose phthalate, and the like.

As used herein, the term "magnesium" refers to the magnesium ion, $Mg^{2+}$.

As used herein, the term "pharmaceutically acceptable solvent" can refer to water, water for injection, aqueous buffer solutions that are physiologically compatible, or aqueous solutions containing organic solvents that are physiologically compatible. A non-comprehensive list of pharmaceutically acceptable solvents is provided in U.S. Department of Health & Human Services, Food & Drug Administration, "Guidance for Industry: Q3C Impurities: Residual Solvents," December 1997 or its current issue.

As used herein, the term "bioavailability" refers to the amount of a substance that is absorbed in the intestines and ultimately available for biological activity in a subject's tissue and cells.

As used herein, the term "enhancing the bioavailability" and the like are used herein to refer to obtaining a desired pharmacological and/or physiological effect of increasing the amount of D-biotin that is absorbed from the intestine or is taken up by tissues and cells after administration of a composition to a mammal, which does not occur naturally.

The effect may be prophylactic in terms of preventing or partially preventing the incidence, risk, or severity of an adverse symptom or condition caused by or related to the deficiency of a therapeutic agent.

As used herein, the terms "preventing", "treating", "treatment" and the like are used herein to generally refer to obtaining a desired pharmacological and physiological effect, and can also refer to a nutritional or nutraceutical effect, the scopes and meanings of which will be clear to the skilled artisan based upon the context in which these terms are used. The effect may be prophylactic in terms of preventing or partially preventing a disease, symptom or condition thereof and/or may be therapeutic in terms of a partial or complete cure of a disease, condition, symptom or adverse effect attributed to the disease. The term "treatment" as used herein encompasses any treatment of a disease in a mammal, particularly a human and includes: (a) preventing the disease from occurring in a subject which may be predisposed to the disease but has not yet been diagnosed as having it; (b) inhibiting the disease or arresting its development; or (c) relieving the disease, causing regression of the disease and/or its symptoms, conditions, and co-morbidities. The terms "optimum" or "healthy" and the like may be used to refer to the physiological amounts of biotin in a mammal, wherein administration of compositions as described herein may be administered to a mammal that may not have a disease or symptoms of a disease associated with reduced D-biotin levels, but may be administered to maintain healthy or optimum amounts of D-biotin along with the other physiological results described herein.

As used herein, the term "therapeutically effective" or "effective" is intended to qualify the amounts of a magnesium D-biotinate composition which will achieve the goal of providing the quantity of D-biotin needed to prevent and treat adverse effects associated with biotin deficiency. In some aspects, an "effective" amount may be the amount that is effective to maintain a healthy amount of D-biotin or maintain optimum amounts of D-biotin. In some embodiments, an "effective" amount may be administered to a mammal that is not experiencing the effects of a disease or other malady affecting D-biotin levels or other biologic aspects as described herein, but an "effective" amount may be that amount that achieves an increase in carboxylase activity and/or increases in cellular energy production (e.g., enhanced cellular mitochondrial activity) in a way that is not achieved through the natural diet or through other supplement regimes. The amounts of a magnesium D-biotinate composition may be administered orally to a subject as part of the same unit dose or as different unit doses administered in a coordinated manner. Further, the amounts of a magnesium D-biotinate composition may be administered in a coordinated manner by different routes of administration, if required to ensure bioavailability in a subject requiring this treatment. By way of example, administration in a coordinated manner may comprise oral administration of an effective amount of a magnesium D-biotinate composition at a time point and administration of an effective amount of a magnesium D-biotinate by oral, transdermal, or intravenous administration at a separate time point within 72 hours of administration of the first effective amount of said composition.

As used herein, the term "excipient material" refers to any compound that is part of a formulation that is not an active ingredient, i.e., one that has no relevant biological activity, and which is added to the formulation to provide specific characteristics to the dosage form, including by way of example, providing protection to the active ingredient from chemical degradation, facilitating release of a tablet or caplet from equipment in which it is formed, and so forth.

For the purpose of this disclosure, a warm-blooded animal is a member of the animal kingdom which includes but is not limited to mammals and birds. In certain embodiments described herein, a mammal may be a horse. The most preferred mammal of this application is human.

To provide a more concise description, some of the quantitative expressions given herein are not qualified with the term "about." It is understood that whether the term "about" is used explicitly or not, every quantity given herein is meant to refer to the actual given value, and it is also meant to refer to the approximation to such given value that would reasonably be inferred based on the ordinary skill in the art, including approximations due to the experimental and/or measurement conditions for such given value.

In order to enable preparative process monitoring, as well as to meet quality and purity requirements for the final product, an example of a process for the preparation of magnesium biotinate involves reaction of a solution of biotin with a solution of a magnesium compound. As shown in Table 1, none of the common solvents were useful for preparation of a solution of biotin, since the solubility of biotin in each solvent is so limited that unwieldy volumes of solvent would be required. See Su et al., *J. Chem. Eng. Data*, 59:3894-3899 (2014).

TABLE 1

Solubility of D-Biotin & Magnesium Compounds in Common Solvents

| Solvent | Biotin | Magnesium Compound |
|---|---|---|
| Water | 22 mg/100 mL | MgO insoluble; Mg salts soluble |
| Ethanol | 80 mg/100 mL | MgO insoluble; Mg salts slightly sol. |
| Methanol | 80 mg/100 mL | MgO insoluble; Mg salts slightly sol. |
| N,N-Dimethylformamide (DMF) | 170 mg/100 mL | MgO insoluble; Mg salts slightly sol. |
| Dimethyl sulfoxide (DMSO) | 4.9 g/100 mL | MgO insoluble; Mg salts slightly sol. |
| Benzene | Soluble | MgO and Mg salts insoluble |

A synthetic approach was developed in an attempt to minimize the volume of a pharmaceutically acceptable solvent that was required to solubilize biotin, thus producing the unnaturally occurring products described herein. Such a pharmaceutically acceptable solvent for biotin would preferably be compatible with solutions of magnesium salts to enable use of pharmaceutically acceptable solvents throughout the preparation. It was thus discovered that biotin could readily and completely be dissolved in a minimum volume of water by adding a water-soluble base, such as ammonium hydroxide, sodium hydroxide, potassium hydroxide, lithium hydroxide, cesium hydroxide, or amines. A clear solution of D-biotinate in a minimum volume of water was thus obtained. No racemization was observed. It was also discovered that magnesium salts such as magnesium bromide and its hydrates, magnesium chloride and its hydrates, magnesium nitrate, and so forth could be dissolved in a minimum volume of water to provide clear and colorless solutions.

Surprisingly, when clear and colorless solutions of a magnesium salt in water were added to clear solutions of D-biotin in water in molar ratios of 0.45-0.55 mole of magnesium to 1 mole of D-biotin, a clear solution was obtained, indicating that the magnesium D-biotinate thus formed was unexpectedly soluble in water. Precipitation of magnesium D-biotinate could be induced by addition of a water-miscible co-solvent, such as acetonitrile or acetone. Methanol or ethanol failed to induce precipitation of magnesium D-biotinate. A determination of the optical rotation of magnesium D-biotinate confirmed that no racemization had taken place.

In some aspects, a method for preparing a magnesium D-biotinate comprises adding a mole equivalent of D-biotin in water and a one-half mole equivalent of a magnesium alkoxide. This reaction was slow until the reaction mixture was heated, whereupon the magnesium alkoxide reacted with D-biotin to form a clear solution of magnesium D-biotinate. When the reaction was complete, no precipitate formed, even when a co-solvent was added. The magnesium D-biotinate composition was isolated by removing the water, washing the remaining solid with ethanol, and drying at 108° C.

Unexpectedly, the magnesium D-biotinate composition was not hygroscopic and was stable upon exposure to light. Compositions were also stable during storage at 25° C./40% relative humidity as well as at 40° C./75% relative humidity.

Some embodiments disclosed herein are based, at least in part, on the surprising and unexpectedly superior finding that the magnesium D-biotinate composition of the present disclosure provides unexpectedly and unnaturally greater quantities of D-biotin after administration. Thus, in some aspects, the magnesium D-biotinate composition increases the bioavailability of biotin when compared to other known compositions. While not wishing to be bound to any particular hypothesis or theory, it is believed that the composition disclosed herein provides unexpectedly greater quantities of D-biotin because of its significantly greater solubility in water and other aqueous solutions. Biotin may be taken up from the intestine by specific interactions of soluble D-biotinate with intestinal sodium-dependent vitamin transporters (SMVT) and by non-specific interactions of soluble D-biotinate with monocarboxylate transporters in the intestine. A magnesium D-biotinate composition of the application provides both magnesium ion and D-biotinate anion in solution (i.e., both soluble magnesium ion and soluble D-biotinate anion). Thus, both moieties are available for physiological uptake via receptors in the intestine. In some aspects, the presently disclosed compositions thus provide more bioavailable biotin than previous compositions.

Compositions capable of delivering more bioavailable biotin may result in compositions having less amounts of total biotin than previous composition and formulations. In this way, manufacturing costs may be decreased and subjects may be administered compositions comprising lower amounts of biotin to achieve similar efficacy to compositions with more biotin. Improved methods of manufacture may be attributed to the new methods of manufacturing relying on water as opposed to traditional methods that rely on organic solvents to produce D-biotin. Producing magnesium biotinate using water as described by the methods contained herein as opposed to organic solvents produces reaction conditions that do not lead to racemization. Without being bound by any particular theory, L-biotin is not bioactive, and thus, producing a pure product containing magnesium D-biotinate is a surprising and improved result. Production of biotin compounds using organic solvents as in the prior art leads to racemic mixtures and can create inactive L-forms of biotin. The methods described herein thus advantageously describe a method that is cheaper and safer and produces an improved unnatural product that can achieve the unnatural and unexpected results described herein.

Since these same transporters also mediate intracellular transport of the vitamin, it is believed that a magnesium D-biotinate composition of the application provides unexpectedly and unnaturally greater quantities of D-biotin after parenteral administration as a physiologically compatible solution because of the significantly higher solubility of magnesium D-biotinate in serum and bodily fluids. In some aspects, the magnesium biotinate is washed to remove substantially all sodium chloride and/or other salts.

The administration of one or more of the compositions disclosed herein can be by any of the methods of administration described herein or by delivery methods known by one of skill in the art. The compositions may be administered orally, through parenteral nutrition, e.g., feeding tube, intravenously, or topically, and through other known means.

For oral administration, the compositions disclosed herein can be provided as a tablet, aqueous or oil suspension, dispersible powder or granule, emulsion, hard or soft capsule, syrup, elixir, or beverage. Solid dosage forms such as tablets and capsules may be comprise an enteric coating. Compositions intended for oral use can be prepared according to any method known in the art for the manufacture of pharmaceutically acceptable compositions and such compositions may include one or more of the following agents: sweeteners, flavoring agents, coloring agents, coatings, and preservatives. The sweetening and flavoring agents will increase the palatability of the preparation. Tablets containing the complexes in admixture with non-toxic pharmaceutically acceptable excipients suitable for tablet manufacture are acceptable. Pharmaceutically acceptable vehicles such as excipients are compatible with the other ingredients of the formulation (as well as non-injurious to the patient). Such excipients include inert diluents such as calcium carbonate, sodium carbonate, lactose, calcium phosphate or sodium phosphate; granulating and disintegrating agents, such as corn starch or alginic acid; binding agents such as starch, gelatin or acacia; and lubricating agents such as magnesium stearate, stearic acid or talc. Tablets can be uncoated or can be coated by known techniques to delay disintegration and absorption in the gastrointestinal tract and thereby provide a sustained action over a longer period of time. For example, a time delay material such as glyceryl monostearate or glyceryl distearate alone or with a wax can be employed.

Formulations for oral use can also be presented as hard gelatin-containing or non-gelatinous capsules wherein the active ingredient is mixed with an inert solid diluent, for example calcium carbonate, calcium phosphate or kaolin, or as soft gelatin capsules wherein the active ingredient is mixed with water or an oil medium, such as peanut oil, liquid paraffin or olive oil. Aqueous suspensions can contain the complex of the described herein admixed with excipients suitable for the manufacture of aqueous suspensions. Such excipients include suspending agents, dispersing or wetting agents, one or more preservatives, one or more coloring agents, one or more flavoring agents and one or more sweetening agents such as sucrose or saccharin.

Oil suspensions can be formulated by suspending the active ingredient in a vegetable oil, such as arachis oil, olive oil, sesame oil or coconut oil, or in a mineral oil such as liquid paraffin. The oil suspension can contain a thickening agent, such as beeswax, hard paraffin or cetyl alcohol. Sweetening agents, such as those set forth above, and flavoring agents can be added to provide a palatable oral preparation. These compositions can be preserved by an added antioxidant such as ascorbic acid. Dispersible powders and granules suitable for preparation of an aqueous suspension by the addition of water can provide the active ingredient in admixture with a dispersing or wetting agent, a suspending agent, and one or more preservatives. Additional excipients, for example sweetening, flavoring and coloring agents, can also be present.

Syrups and elixirs can be formulated with sweetening agents, such as glycerol, sorbitol or sucrose. Such formulations can also contain a demulcent, a preservative, a flavoring or a coloring agent.

The composition for parenteral administration can be in the form of a sterile injectable preparation, such as a sterile injectable aqueous or oleaginous suspension. This suspension can be formulated according to methods well known in the art using suitable dispersing or wetting agents and suspending agents. The sterile injectable preparation can also be a sterile injectable solution or suspension in a non-toxic parenterally-acceptable diluent or solvent, such as a solution in 1,3-butanediol. Suitable diluents include, for example, water, Ringer's solution and isotonic sodium chloride solution. In addition, sterile fixed oils can be employed conventionally as a solvent or suspending medium. For this purpose, any bland fixed oil can be employed including synthetic mono or diglycerides. In addition, fatty acids such as oleic acid can likewise be used in the preparation of injectable preparations.

It will be appreciated that the amount of the compound may be combined with a carrier material to produce a single dosage form. Such forms will vary depending upon the host treated and the particular mode of administration.

In some aspects, magnesium biotinate may be added to food that is designed for animals. For example, the compound or composition may be added to and/or comprise a pet treat or biscuit, for example, a dog biscuit or a cat treat Aqueous suspensions may contain the compound disclosed herein in admixture with excipients suitable for the manufacture of aqueous suspensions. Such excipients include suspending agents, dispersing or wetting agents, one or more preservatives, one or more coloring agents, one or more flavoring agents and one or more sweetening agents such as sucrose or saccharin.

Controlled release vehicles are well known to those of skill in the pharmaceutical sciences, and these aspects can be applied to nutritional and dietary supplements. The technology and products in this art are variably referred to as controlled release, sustained release, prolonged action, depot, repository, delayed action, retarded release and timed release; the words "controlled release" as used herein is intended to incorporate each of the foregoing technologies.

Numerous controlled release vehicles are known, including biodegradable or bioerodable polymers such as polylactic acid, polyglycolic acid, and regenerated collagen. Known controlled release drug delivery devices include creams, lotions, tablets, capsules, gels, microspheres, liposomes, ocular inserts, minipumps, and other infusion devices such as pumps and syringes. Implantable or injectable polymer matrices, and transdermal formulations, from which active ingredients are slowly released, are also well known and can be used in the disclosed methods.

Controlled release preparations can be achieved by the use of polymers to form complexes with or absorb the magnesium biotinate. The controlled delivery can be exercised by selecting appropriate macromolecules such as polyesters, polyamino acids, polyvinylpyrrolidone, ethylenevinyl acetate, methylcellulose, carboxymethylcellulose, and protamine sulfate, and the concentration of these macromolecule as well as the methods of incorporation are selected in order to control release of active complex.

Controlled release of active complexes can be taken to mean any of the extended release dosage forms. The following terms may be considered to be substantially equivalent to controlled release, for the purposes of the present disclosure: continuous release, controlled release, delayed release, depot, gradual release, long term release, programmed release, prolonged release, programmed release, proportionate release, protracted release, repository, retard, slow release, spaced release, sustained release, time coat, time release, delayed action, extended action, layered time action, long acting, prolonged action, sustained action medications and extended release, release in terms of pH level in the gut and intestine, breakdown of the molecule and based on the absorption and bioavailability.

Hydrogels, wherein magnesium biotinate is dissolved in an aqueous constituent to gradually release over time, can be prepared by copolymerization of hydrophilic mono-olefinic monomers such as ethylene glycol methacrylate. Matrix devices, wherein magnesium biotinate is dispersed in a matrix of carrier material, can be used. The carrier can be porous, non-porous, solid, semi-solid, permeable or impermeable. Alternatively, a device comprising a central reservoir of magnesium biotinate surrounded by a rate controlling membrane can be used to control the release of the complex. Rate controlling membranes include ethylene-vinyl acetate copolymer or butylene terephthalate/polytetramethylene ether terephthalate. Use of silicon rubber or ethylene-vinyl alcohol depots are also contemplated.

Controlled release oral formulations are also well known. In one embodiment, the active complex is incorporated into a soluble or erodible matrix, such as a pill or a lozenge. In another example, the oral formulations can be a liquid used for sublingual administration. These liquid compositions can also be in the form a gel or a paste. Hydrophilic gums, such as hydroxymethylcellulose, are commonly used. A lubricating agent such as magnesium stearate, stearic acid, or calcium stearate can be used to aid in the tableting process.

Magnesium biotinate may also be delivery topically, including in a salve, cream, lotion, ointment, shampoo, cosmetic, or emulsion.

The amount of a complex that will be effective in the treatment of a particular disorder or condition disclosed herein will depend on the nature of the disorder or condition, and can be determined by standard clinical techniques. In addition, in vitro or in vivo assays may optionally be employed to help identify optimal dosage ranges.

The compositions may be administered once, twice, or three times per day. In some aspects, the compositions are administered four times a day. For example, the compositions may be administered before, after, or during a meal. Dosing for oral administration may be with a regimen calling for single daily dose, or for a single dose every other day, or for a single dose within 72 hours of the first administered dose, or for multiple, spaced doses throughout the day. The active agents which make up the therapy may be administered simultaneously, either in a combined dosage form or in separate dosage forms intended for substantially simultaneous oral administration. The active agents which make up the therapy may also be administered sequentially, with either active component being administered by a regimen calling for two-step ingestion. Thus, a regimen may call for sequential administration of the active agents with spaced-apart ingestion of the separate, active agents. The time period between the multiple ingestion steps may range from a few minutes to as long as about 72 hours, depending upon the properties of each active agent such as potency, solubility, bioavailability, plasma half-life and kinetic profile of the agent, as well as depending upon the age and condition of the patient. The active agents of the therapy whether administered simultaneously, substantially simultaneously, or sequentially, may involve a regimen calling for administration of one active agent by oral route and the other active agent by intravenous route. In one aspect, the embodiments described herein achieve a higher solubility than prior D-biotin compositions, and thus, unexpectedly and surprisingly achieve improved abilities for using the compositions for intravenous administration because a more concentrated solution can be produced. Whether the active agents of the therapy are administered by oral or intravenous route, separately or together, each such active agent will be contained in a suitable pharmaceutical formulation of pharmaceutically-acceptable excipients, diluents or other formulations components.

Active ingredients (i.e., magnesium D-biotinate and other pharmaceutical or supplemental ingredients that may be present) can be administered by the oral route in solid dosage forms, such as tablets, capsules, and powders, or in liquid dosage forms, such as elixirs, syrups, and suspensions. Each active ingredient can be administered by the parenteral route in liquid dosage forms. The composition can be made in the form of a dosage unit containing a particular amount of each active ingredient. One example of an oral dosage form of a composition of the present application is an admixture of powders contained within a sachet. Because a composition of the present application is not hygroscopic and has no repugnant taste or odor, the admixture of powders comprising a composition of the present application can be sprinkled on food or stirred into beverages to enhance case of use and support high levels of compliance with daily dosage regimens.

In general, the dosage forms of compositions of this disclosure can be prepared by conventional techniques, as are described in Remington's Pharmaceutical Sciences, a standard reference in this field [Gennaro A R, Ed. Remington: The Science and Practice of Pharmacy. 20th Edition. Baltimore: Lippincott, Williams & Williams, 2000]. For therapeutic purposes, the active components of this combination therapy application can be combined with one or more adjuvants appropriate to the indicated route of administration. The components may be admixed with lactose, sucrose, starch powder, cellulose esters of alkanoic acids, cellulose alkyl esters, talc, stearic acid, magnesium stearate, gelatin, acacia gum, sodium alginate, polyvinylpyrrolidone, and/or polyvinyl alcohol, and then tableted or encapsulated for convenient administration, the amounts of which are ascertainable by the skilled artisan. Such capsules or tablets may contain a controlled-release formulation as may be provided in a dispersion of active compound in hydroxypropyl methylcellulose. Solid dosage forms can be manufactured as sustained release products to provide for continuous release of medication over a period of hours. Compressed tablets can be sugar coated or film coated to mask any unpleasant taste and protect the tablet from the atmosphere, or enteric coated for selective disintegration in the gastrointestinal tract. Both the solid and liquid oral dosage forms can contain coloring and flavoring to increase patient acceptance. Other adjuvants and modes of administration are well and widely known in the pharmaceutical art and these aspects can also be applied to any of the nutritional or dietary supplements described herein.

While the present invention has been described in some detail for purposes of clarity and understanding, one will appreciate that various changes in form and detail can be made without departing from the true scope of the invention.

EXAMPLES

Example 1. Preparation of Magnesium D-Biotinate

According to the Merck Index, 12th Edition, Monograph 1272, biotin exhibits a solubility of 22 mg/100 ml of water, 80 mg/100 mL of ethanol, 1.7 mg/ml of N,N-dimethylformamide, and is insoluble in other common organic solvents. A slurry of D-biotin (4.8 g, 20 mmol) in 15 mL of water was stirred with magnesium oxide (420 mg, 10.5 mmol). Even after days of stirring, both at ambient and elevated temperatures, a clear solution was not obtained, and thus these methods are not reasonable methods to prepare magnesium D-biotinate.

Example 2. Preparation A of Magnesium D-Biotinate

D-Biotin (2.44 g, 10 mmol) was suspended in 10 ml of water and 10 mL of 1 N sodium hydroxide solution (NaOH; 10 mmol) was added. Magnesium chloride hexahydrate ($MgCl_2 \cdot 6\ H_2O$; 1.01 g; 0.05 mmol) was dissolved in 2 mL of water, and the resulting solution was added to the aqueous sodium biotinate. Aliquots of the solution were removed, and four co-solvents were evaluated.

Addition of approximately 10 mL methanol to 1 mL of the magnesium biotinate solution formed a clear solution. Alternatively, addition of approximately 10 mL ethanol to 1 mL of the magnesium biotinate solution formed a clear solution. Addition of approximately 7 mL acetonitrile to 1 mL of the magnesium biotinate solution formed a cloudy solution with a white precipitate. Addition of approximately 7 mL acetone to 1 mL of the magnesium biotinate solution formed a white precipitate.

The experiment was repeated at the same scale. After the clear solution of magnesium biotinate was obtained, about three volumes of acetone were added. The resulting precipitate was isolated by filtration and washed with acetone:water (4:1), and then dried under vacuum to provide 2.9 g (95%) of amorphous magnesium D-biotinate.

Example 3. Preparation B of Magnesium D-Biotinate

D-Biotin (2.44 g, 1 mmol) was added to 50 mL of 2 M ammonium hydroxide solution. Magnesium chloride hexahydrate ($MgCl_2 \cdot 6\ H_2O$; 1.01 g; 0.05 mmol) was dissolved in 2 mL of water and added to the sodium biotinate solution. Five volumes of acetone were added and the precipitate was isolated by filtration and washed with acetone:water (4:1), and then dried under vacuum to provide 1.9 g (62%) of amorphous magnesium D-biotinate.

Example 4. Preparation C of Magnesium D-Biotinate

A minimum volume (approximately 14 mL) of 1 N NaOH was added to D-biotin (24.4 g, 100 mmol) to provide a clear solution. The solution was filtered. $MgCl_2 \cdot 6\ H_2O$ (10.17 g; 50 mmol) was dissolved in a minimum volume of water, and added to the sodium biotinate solution. Acetone (400 mL) was added, and the precipitate was isolated by filtration and washed with 200 mL of acetone:water (4:1), and then dried under vacuum to provide 24.5 g (96%) of amorphous magnesium D-biotinate. The solubility of magnesium D-biotinate is at least about 10 g/L.

Example 5. Stability of Magnesium D-Biotinate

Magnesium biotinate compositions of the invention were stable during storage at room temperature. The amorphous solid was not hygroscopic, as measured by weight, and showed no signs of degradation after 30 days at 40% relative humidity and 25° C. and after 30 days at 75% relative humidity and 40° C. The amorphous solid did not change color on exposure to light.

Example 6. Preparation D: Crystalline Magnesium D-Biotinate

A minimum volume (approximately 14 mL) of 1 N NaOH was added to D-biotin (24.4 g, 100 mmol) to provide a clear solution. $MgCl_2 \cdot 6 H_2O$ (10.17 g; 50 mmol) was dissolved in a minimum volume of water, and added to the sodium biotinate solution. Acetone (400 mL) was added, and the precipitate was isolated by filtration and washed with 200 mL of acetone:water (4:1), and then dried under vacuum.

Example 7. Preparation E of Magnesium D-Biotinate

D-Biotin (2.44 g, 1 mmol) was suspended in 80 mL of water. Magnesium ethoxide (560 mg, 5 mmol) was added. The resulting slurry was stirred for 1 hr at 80° C. until the suspension became a clear solution. The water was removed by evaporation or lyophilization. The solid thus formed was washed with ethanol, and dried between 100-110° C., providing 1.9 g (62%) of amorphous magnesium D-biotinate.

Example 8. Large Scale Preparation I of Magnesium D-Biotinate

Figure 3:
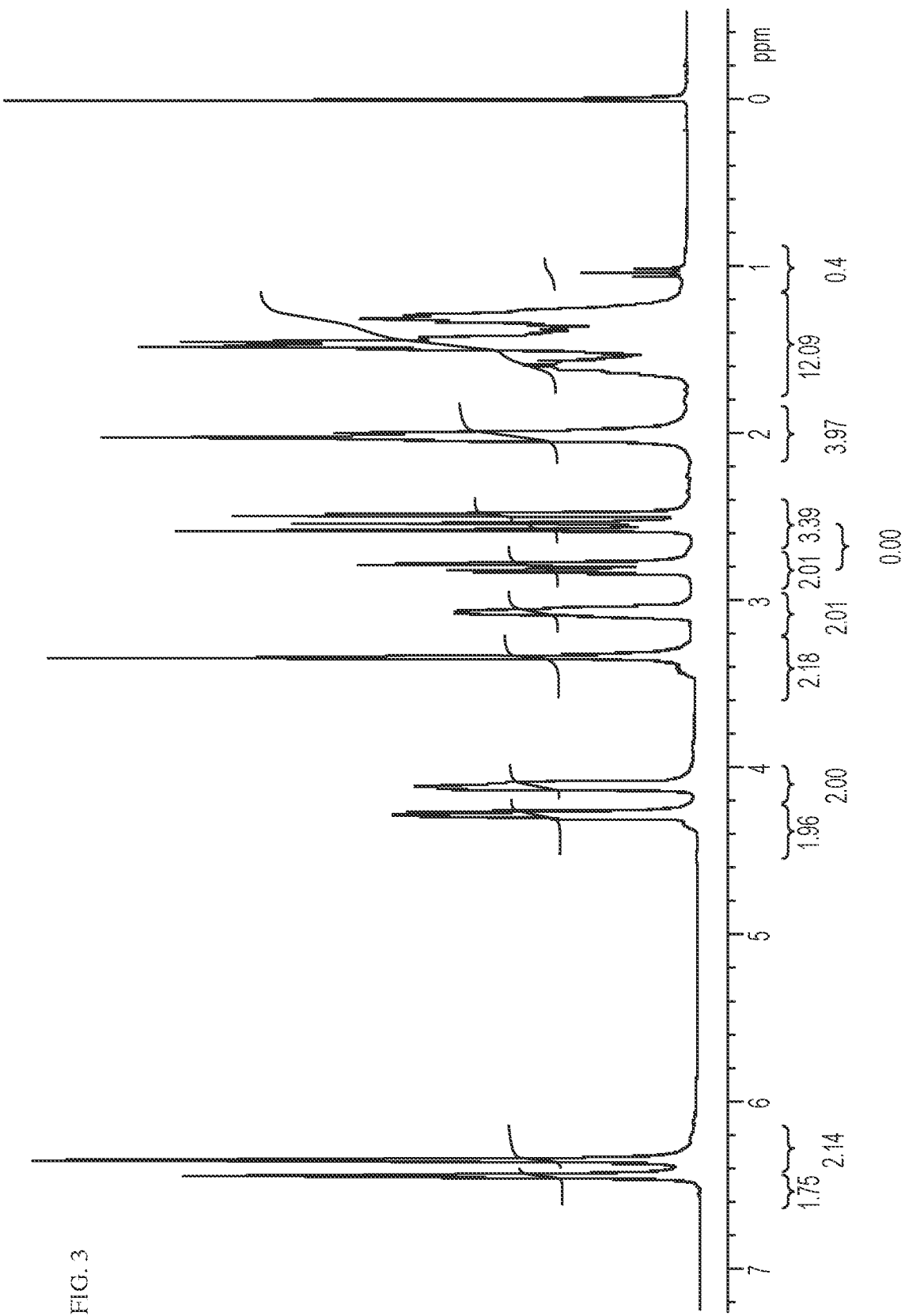
FIG. 3 depicts a $^1$H-NMR spectrum of a magnesium D-biotinate which was prepared as described in Example 8.
Figure 4A:
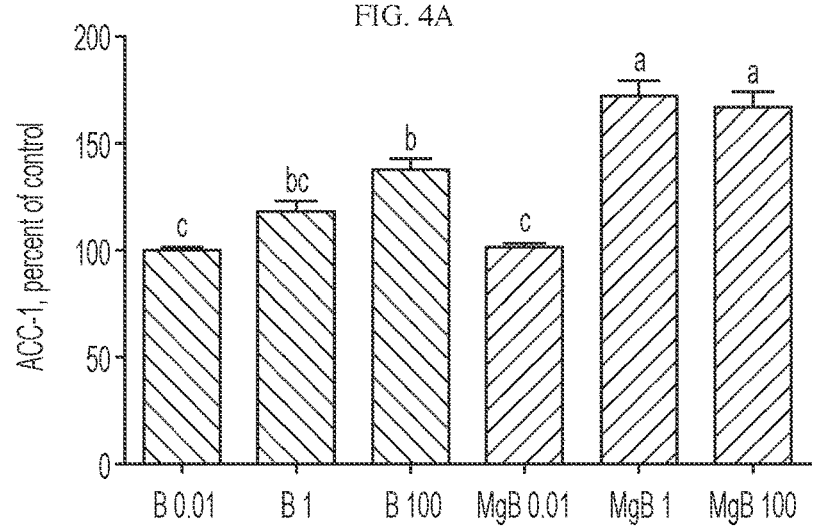
FIGS. 4A and 4B show unexpectedly improved acetyl-CoA carboxylase ACC-1 and ACC-2 activity, respectively.
Figure 4B:
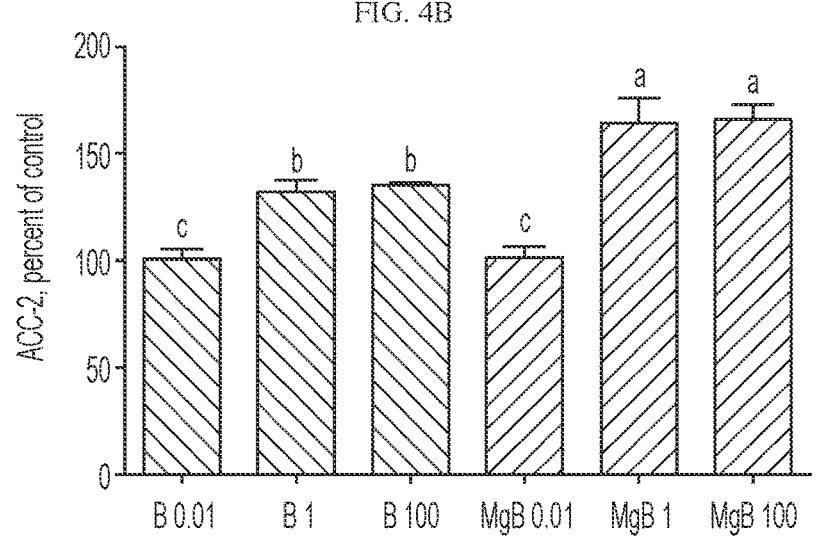
Figure 4C:
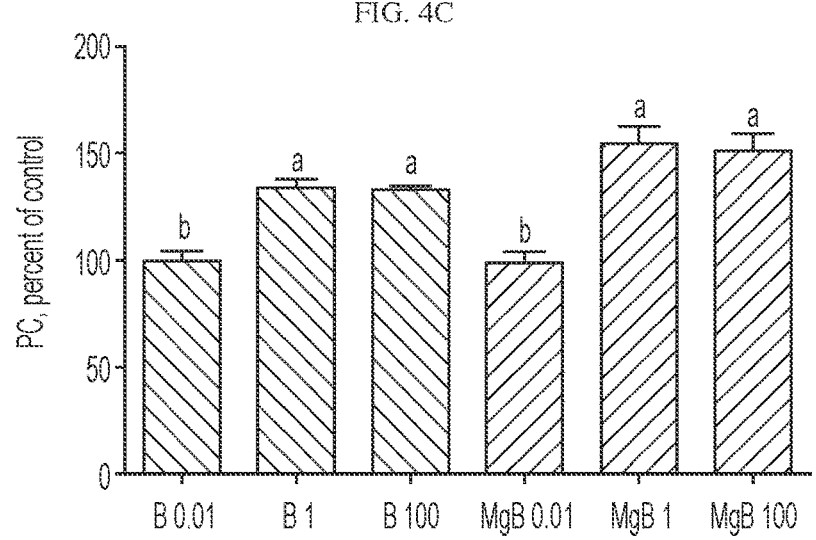
FIG. 4C shows unexpectedly improved pyruvate carboxylase (PC) activity.
Figure 4D:
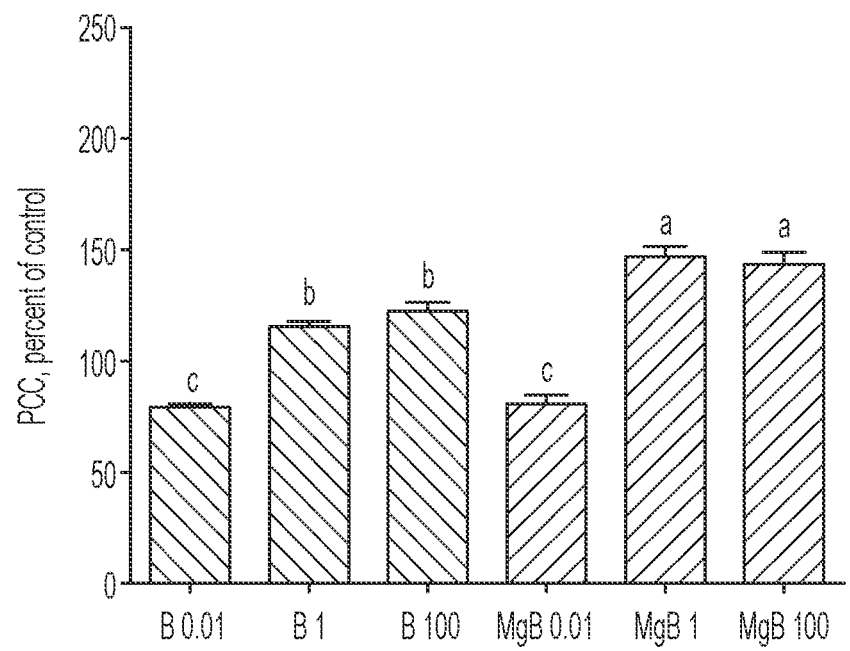
FIG. 4D shows the unexpectedly improved propionyl-CoA carboxylase (PCC) activity.
Figure 4E:
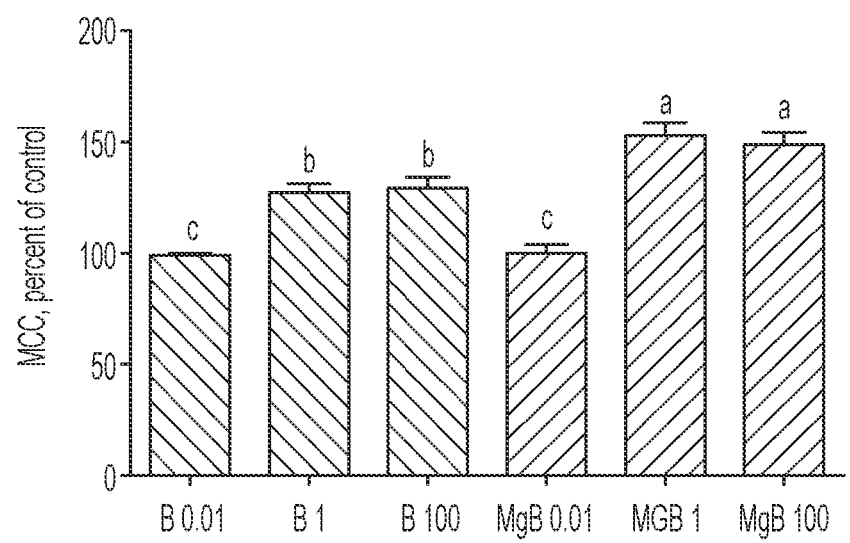
FIG. 4E shows the unexpectedly improved methylcrotonyl-CoA carboxylase (MCC) activity.

Approximately 128 mL of 1 N NaOH was added to D-biotin (30 g, 123 mmol) to provide a clear solution which was then filtered. $MgCl_2 \cdot 6 H_2O$ (13.1 g; 64 mmol) was dissolved in 10 mL water and added to the sodium biotinate solution. Acetone (750 mL) was added and the resulting precipitate was isolated by filtration. The filter cake was suspended in 500 mL 95% ethanol, filtered, and air-dried, followed by drying under vacuum at 108° C. to provide 23.8 g (73.6%) of magnesium D-biotinate. Elemental analysis: 3.9% by weight, Mg and 0.6% by weight sodium (as NaCl). The NMR spectrum of magnesium D-biotinate is shown in FIG. 3. A specific rotation of +77.3° (water; 25° C.) was observed.

Example 9. Large Scale Preparation II of Magnesium D-Biotinate

Figure 2:
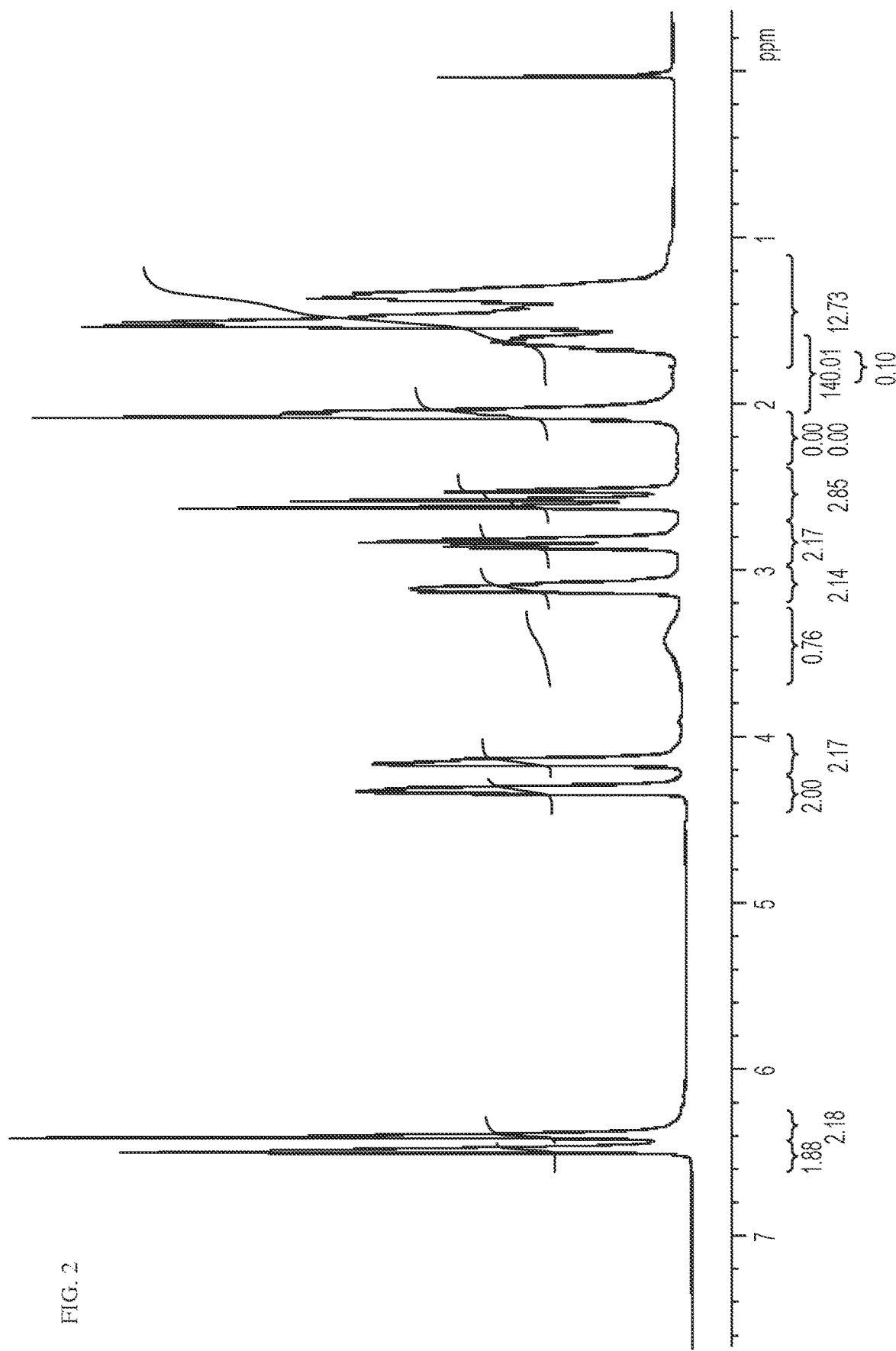
FIG. 2 depicts a 1H-NMR spectrum of a magnesium D-biotinate which was prepared as described in Example 9.

D-Biotin (9.8 g, 40 mmol) was suspended in 200 ml of water. Magnesium ethoxide (2.5 g, 22 mmol) was added and the resulting slurry heated to approximately 80° C. The resulting clear solution was filtered and water was removed by evaporation under vacuum. The solid was air-dried. This reaction was repeated twice and the combined solids isolated from the three reactions were dried under vacuum at 100-110° C. to provide 29 g (94.8%) of amorphous magnesium D-biotinate. Elemental analysis: 3.9% by weight, Mg. The NMR spectrum of magnesium D-biotinate is shown in FIG. 2. The solubility of magnesium D-biotinate was estimated at 1 g/100 mL. A specific rotation of +75.1° (water; 25° C.) was observed.

Example 10. Determination of Optical Rotation and Verification of Absence of Racemization The optical rotation of an aqueous solution of 1 g of magnesium D-biotinate per 100 mL was determined with a path length of 100 mm and a temperature of 25° C. A wavelength of incident light of 589 nm was used. The optical rotation of a sample of magnesium D-biotinate obtained from Example 8 was determined to be +77.3°. This was designated the reference value. The optical rotation of a sample of magnesium D-biotinate prepared Example 9 was +75.1° (under identical test conditions). Accordingly, no racemization occurred under either set of conditions.

Example 11. Magnesium D-Biotinate-Serum Biotin Levels

In a double-blind clinical study, 30 subjects are divided into two groups (n=15). The control group receives a supplement containing 956 mg D-biotin and 37 mg of magnesium as magnesium oxide. The trial group receives a supplement containing 500 mg of magnesium D-biotinate (22 mg of magnesium and 478 mg of biotin), or one-half the total dose of biotin and magnesium of the control group. Serum levels of biotin (ng/ml) are measured at one hour, four hours, six hours, and eight hours. The mean serum biotin levels for the trial group are between 80-120% of the control group at each time point. Thus, magnesium D-biotinate provides 80-120% of bioavailable biotin relative to twice the dose of D-biotin alone (i.e., administered as an independent component in a formulation containing magnesium as magnesium oxide).

Example 12. Magnesium D-Biotinate—Biotin $C_{max}$ and $T_{max}$

In a double-blind clinical study, 30 subjects are divided into two groups (n=15). The control group receives a supplement containing 956 mg biotin and 37 mg of magnesium as magnesium oxide. The trial group receives a supplement containing 500 mg of magnesium D-biotinate (22 mg of magnesium and 478 mg of biotin), or one-half the total dose of biotin and magnesium of the control group. Biotin $C_{max}$ (ng/ml) and $T_{max}$ (minutes) are measured in each subject. The mean biotin $C_{max}$ for the trial group are between 80-120% of the control group at each time point. Thus, magnesium D-biotinate provides 80-120% of the maximum serum concentration of biotin relative to twice the dose of biotin alone (i.e., administered as an independent component in a formulation containing magnesium as magnesium oxide). The mean biotin $T_{max}$ for the trial group are between 50-80% of the control group at each time point. Thus, magnesium D-biotinate the maximum amount of bioavailable biotin in 50-80% less time relative to twice the dose of biotin alone (i.e., administered as an independent component in a formulation containing magnesium as magnesium oxide).

Example 13. Magnesium D-Biotinate—Biotin Area Under the Curve ($AUC_{0 \rightarrow \infty}$)

In a double-blind clinical study, 30 subjects are divided into two groups (n=15). The control group receives a supplement containing 956 mg biotin and 37 mg of magnesium as magnesium oxide. The trial group receives a supplement containing 500 mg of magnesium D-biotinate (22 mg of magnesium and 478 mg of biotin), or one-half the total dose of biotin and magnesium of the control group. Biotin $AUC_{0\to\infty}$ (ng·h/mL) are measured in each subject. The mean biotin $AUC_{0\to\infty}$ for the trial group are between 80-120% of the control group at each time point. Thus, magnesium D-biotinate provides 80-120% of the maximum amount of bioavailable biotin relative to twice the dose of biotin alone (i.e., administered as an independent component in a formulation containing magnesium as magnesium oxide).

Example 14. Magnesium D-Biotinate—Sustained Release

In a double-blind clinical study, 30 subjects are divided into two groups (n=15). The control group receives an enteric-coated multilayer tablet containing 956 mg biotin and 37 mg of magnesium as magnesium oxide. The trial group receives an enteric-coated multilayer tablet containing 500 mg of magnesium D-biotinate (22 mg of magnesium and 478 mg of biotin), or one-half the total dose of biotin and magnesium of the control group.

The biotin $C_{max}$ (ng/ml); $T_{max}$ (minutes); and $AUC_{0\to\infty}$ (ng·h/mL) are measured in each subject. The values for $C_{max}$, $T_{max}$, and $AUC_{0\to\infty}$ show a first peak in serum biotin levels, followed by a first plateau of relatively constant blood serum biotin levels, followed by a second peak in serum biotin levels, followed by a second plateau of relatively constant blood serum biotin levels. In each instance, the mean biotin $C_{max}$ and $AUC_{0\to\infty}$ are between 80-120% of the control group at each time point, and the mean $T_{max}$ are between 50-80% of the control group at each time point. Thus, the multilayer enteric-coated magnesium D-biotinate formulation is capable of delivering 80-120% of the maximum serum biotin concentration and 80-120% of the maximum amount of bioavailable biotin, in 50-80% percent of the time, relative to twice the dose of biotin alone (i.e., administered as an independent component in a formulation containing magnesium as magnesium oxide).

Example 15. Absorption Results of Magnesium Biotinate Administration

In a study, biotin and magnesium biotinate was administered to male Sprague-Dawley rats. The male Sprague-Dawley rats were reared at the temperature of 22±2 C, humidity of 55±5% and with a 12 h light-12 h dark cycle. A standard diet was used with minor modification commonly used for the analysis of dietary components formulated by the American Institute of Nutrition. The diet was modified to include spray-dried egg white as its sole protein source. Avidin protein in egg white binds 1.44 mg biotin/kg of purified diet, inhibiting biotin absorption. The level of dietary biotin designated in this study represented biotin in excess of the binding capacity of the dietary egg white avidin. Rats were randomly assigned to a standard diet-based egg white powdered diet containing one of the following biotin concentrations (N=7 per group):

1. Group I (Control) (B 0): rats were fed a standard diet and supplemented with 0.01 mg commercial biotin (d-biotin)/kg body weight;
2. Group II (Control) (B 1): rats were fed a standard diet and supplemented with 1 mg biotin (d-biotin)/kg body weight;
3. Group III (Control) (B 100): rats were fed a standard diet and supplemented with 100 mg biotin (d-biotin)/kg body weight;
4. Group IV (MgB 0): rats were fed a standard diet and supplemented with 0.01 mg magnesium biotinate/kg body weight;
5. Group V (MgB 1): rats were fed a standard diet and supplemented with 1 mg magnesium biotinate/kg body weight;
6. Group VI (MgB 100): rats were be fed with standard diet and supplemented with 100 mg magnesium biotinate/kg body weight.

The duration of the study was 30 days and a summary of the results is presented in Table 2 below:

TABLE 2

| Items | Groups | | | | | | -- P -- |
|---|---|---|---|---|---|---|---|
| | B 0.01 | B 1 | B 100 | MgB 0.01 | MgB 1 | MgB 100 | |
| Serum Biotin, nmol/L | 23.65 ± 2.60$^c$ | 136.67 ± 2.73$^c$ | 3517.14 ± 87.93$^b$ | 23.41 ± 2.31$^c$ | 171.13 ± 3.02$^c$ | 5161.43 ± 250.96$^a$ | 0.0001 |
| Liver Biotin, nmol/g | 0.02 ± 0.01$^e$ | 0.56 ± 0.04$^d$ | 1.38 ± 0.02$^b$ | 0.03 ± 0.01$^e$ | 0.71 ± 0.03$^c$ | 1.62 ± 0.02$^a$ | 0.0001 |
| Brain Biotin, nmol/g | 0.14 ± 0.01$^e$ | 0.42 ± 0.05$^d$ | 1.37 ± 0.04$^b$ | 0.14 ± 0.01$^e$ | 0.66 ± 0.04$^c$ | 1.65 ± 0.03$^a$ | 0.0001 |
| Liver cGMP, pmol/mg protein | 8.46 ± 0.26$^d$ | 12.01 ± 0.26$^c$ | 14.68 ± 0.32$^b$ | 8.60 ± 0.28$^d$ | 13.04 ± 0.98$^{bc}$ | 17.07 ± 0.28$^a$ | 0.0001 |

Data are means ± SE.
Different superscripts (a-e) indicate group mean differences (p < 0.05).

Additional results are shown in FIG. 4, showing the results of administration of magnesium biotinate compared to administration of biotin. B 0.01 and MgB 0.01 correspond with administration of 0.01 mg/kg body weight of biotin and magnesium biotinate, respectively. B 1 and MgB 1 correspond with administration of 1 mg/kg of body weight of biotin and magnesium biotinate respectively. B 100 and MgB 100 correspond with administration of 100 mg/kg of body weight of biotin and magnesium biotinate respectively. FIGS. 4A and 4B show unexpectedly improved acetyl-CoA carboxylase ACC-1 and ACC-2 activity, respectively. FIG. 4C shows unexpectedly improved pyruvate carboxylase (PC) activity. FIG. 4D shows unexpectedly improved propionyl-CoA carboxylase (PCC) activity. FIG. 4E shows unexpectedly improved methylcrotonyl-CoA carboxylase (MCC) activity. These results also demonstrate the surprising results that not only does magnesium biotinate have a significantly improved solubility, but it also has higher absorption, which is a counterintuitive unexpected result. These results thus indicate that the compositions described herein are both useful for mammals with biotin deficiency and that administering magnesium biotinate to mammals that are not experiencing biotin deficiency may achieve improved carboxylase function and the other improved results as described herein.

Example 16. Mitochondrial Metabolic Activity

In this example, the relative mitochondrial activity of biotin-starved cell cultures was compared to that of peripheral blood mononuclear cells (PBMC) that were supplied with either D-biotin or magnesium biotinate. The untreated cells received no treatment while the other cells were supplied with doses of 0.05 mg/L of D-biotin or magnesium biotinate, which were exposed to serial dilutions of these for 24 hours after which time the cultures were processed in a colorimetric MTT assay. The results are shown in FIG. 5 and demonstrate that the magnesium biotinate administration achieved a highly improved, unexpected, and significant result over the D-biotin administration. These results reflect the sum of the metabolic activities of each cell culture. FIG. 5 shows the colorimetric readings as the average +/−standard deviation for each triplicate set of cell cultures, compared to untreated cell cultures. The statistical significance for within treatment analysis is indicated by "*" ($P<0.05$) while statistical significance for between treatments is indicated by "##" ($P<0.01$).

The above description discloses several methods and materials of the present invention. This invention is susceptible to modifications in the methods and materials, as well as alterations in the fabrication methods and equipment. Such modifications will become apparent to those skilled in the art from a consideration of this disclosure or practice of the invention disclosed herein. Consequently, it is not intended that this invention be limited to the specific embodiments disclosed herein, but that it cover all modifications and alternatives coming within the true scope and spirit of the invention.

When introducing elements of the present application or the preferred embodiment(s) thereof, the articles "a", "an", "the" and "said" are intended to mean that there are one or more of the elements. The terms "comprising", "including" and "having" are intended to be inclusive and mean that there may be additional elements other than the listed elements.

Without further elaboration, it is believed that one skilled in the art can, using the preceding description, utilize the present disclosure to its fullest extent. The specific embodiments are, therefore, to be construed as merely illustrative, and not limitative of the remainder of the disclosure in any way whatsoever. While the present disclosure has been described in some detail for purposes of clarity and understanding, one will appreciate that various changes in form and detail can be made without departing from the true scope of the application.

All references cited herein, including but not limited to published and unpublished applications, patents, and literature references, are incorporated herein by reference in their entirety and are hereby made a part of this specification. To the extent publications and patents or patent applications incorporated by reference contradict the disclosure contained in the specification, the specification is intended to supersede and/or take precedence over any such contradictory material.

What is claimed is:

1. A method of reducing hair loss, improving hair strength, improving hair texture, or a combination thereof in a mammal comprising orally administering a composition comprising an effective amount of isolated crystalline or isolated amorphous magnesium biotinate to the mammal.

2. The method of claim 1, wherein the mammal has a condition selected from alopecia, excessive hair loss, thin hair, rough hair, brittle hair, or weak hair.

3. The method of claim 1, wherein the mammal is a human.

4. The method of claim 1, wherein the magnesium biotinate is enriched with respect to the D-enantiomer, or wherein the magnesium biotinate is magnesium D-biotinate.

5. The method of claim 1, wherein the magnesium biotinate is not hygroscopic.

6. The method of claim 1, wherein the effective amount is from about 10 mg to about 100 mg of the isolated crystalline or isolated amorphous magnesium biotinate.

7. The method of claim 1, wherein the composition further comprises an additional therapeutic agent.

* * * * *